United States Patent [19]

Lazo et al.

[11] Patent Number: 5,420,228

[45] Date of Patent: May 30, 1995

[54] FLUORESCENT-LABELLED BLEOMYCIN ANALOGUES

[75] Inventors: John S. Lazo; Jehangir S. Mistry, both of Pittsburgh; Jitesh P. Jani, McKees Rock; Said M. Sebti, Pittsburgh, all of Pa.

[73] Assignee: University of Pittsburgh of the Commonwealth System of Higher Education, Pittsburgh, Pa.

[21] Appl. No.: 182,862

[22] Filed: Jan. 14, 1994

Related U.S. Application Data

[63] Continuation of Ser. No. 881,414, May 11, 1992, abandoned, which is a continuation-in-part of Ser. No. 681,158, Apr. 5, 1991, abandoned.

[51] Int. Cl.$^6$ .............................. C07K 9/00; C07K 3/28
[52] U.S. Cl. ..................................... 530/322; 530/345
[58] Field of Search ................... 530/322, 345; 549/223

[56] References Cited

U.S. PATENT DOCUMENTS

| | | | |
|---|---|---|---|
| 3,922,262 | 11/1975 | Umezawa et al. | 530/322 |
| 4,246,400 | 1/1981 | Miyaki et al. | 536/16.8 |
| 4,318,846 | 3/1982 | Khanna et al. | 549/223 |
| 4,791,069 | 12/1988 | Hovorka et al. | 436/534 |
| 4,894,348 | 1/1990 | Robert et al. | 549/223 |

OTHER PUBLICATIONS

Windholz et al, *The Merck Index,* 10th ed., monographs 1308,8920, pp. 183, 1299–1300, (1983).
Evrain et al "The Preparation of Three Fluorescat-labeled Derivatives of Testosterone", *Steroids* 35:611–619 (Jun. 1980).
Gaudray et al "Fluorescent Methotrexate Labeling and Flow-Cytometric Analysis . . . " *J. Biol. Chem.* 261:6285–6292 (May 1986).
Broughton et al "Radioimmunoassay of Bleomycin" *Cancer Res* 36:1418–1421 (Apr. 1976).
Broughton et al "A Radioimmunoassay for Tallysomycin" *Cancer Treat. Rep.* 63 (11–12): 1829–1832 (Dec. 1979).
Fujiwara et al "Enzyme Immunoassay for pRepleomycin . . . " Cancer Res. 41:4121–4126 (Oct. 1981).
Smith et al pp. 143–191 in *Modern Fluorescence Spectroscopy,* editor Wehry (1981).
Dolbeare, pp. 251–293 in *Modern Fluorescence Spectroscopy,* editor Wehry (1981).
Broughton et al, "Radioimmunoassay for tallysomycin", *Cancer Treat Rep 63:* 1829–1832, 1979, abstracted in *Biol Abstr 69(12):*AB8456, #79722.
Cantor, C. et al., *Biophysical Chemistry Part II,* pp. 443–446, 1980.
Morris, G. et al., "Cysteine Proteinase Inhibotors And Bleomycin–Sensitive And –Resistant Cells", *Biochemical Pharmacology,* vol. 41, No. 11, pp. 1559–1566, 1991.

*Primary Examiner*—Stephen G. Walsh
*Attorney, Agent, or Firm*—Arnold B. Silverman; Jolene W. Appleman

[57] ABSTRACT

A fluorescent-labelled bleomycin analog useful as a probe for measuring cellular uptake of bleomycin and bleomycin derivatives, including methods of making and using same. The analog may further be used as a therapeutic agent as well as a diagnostic tool.

14 Claims, 6 Drawing Sheets

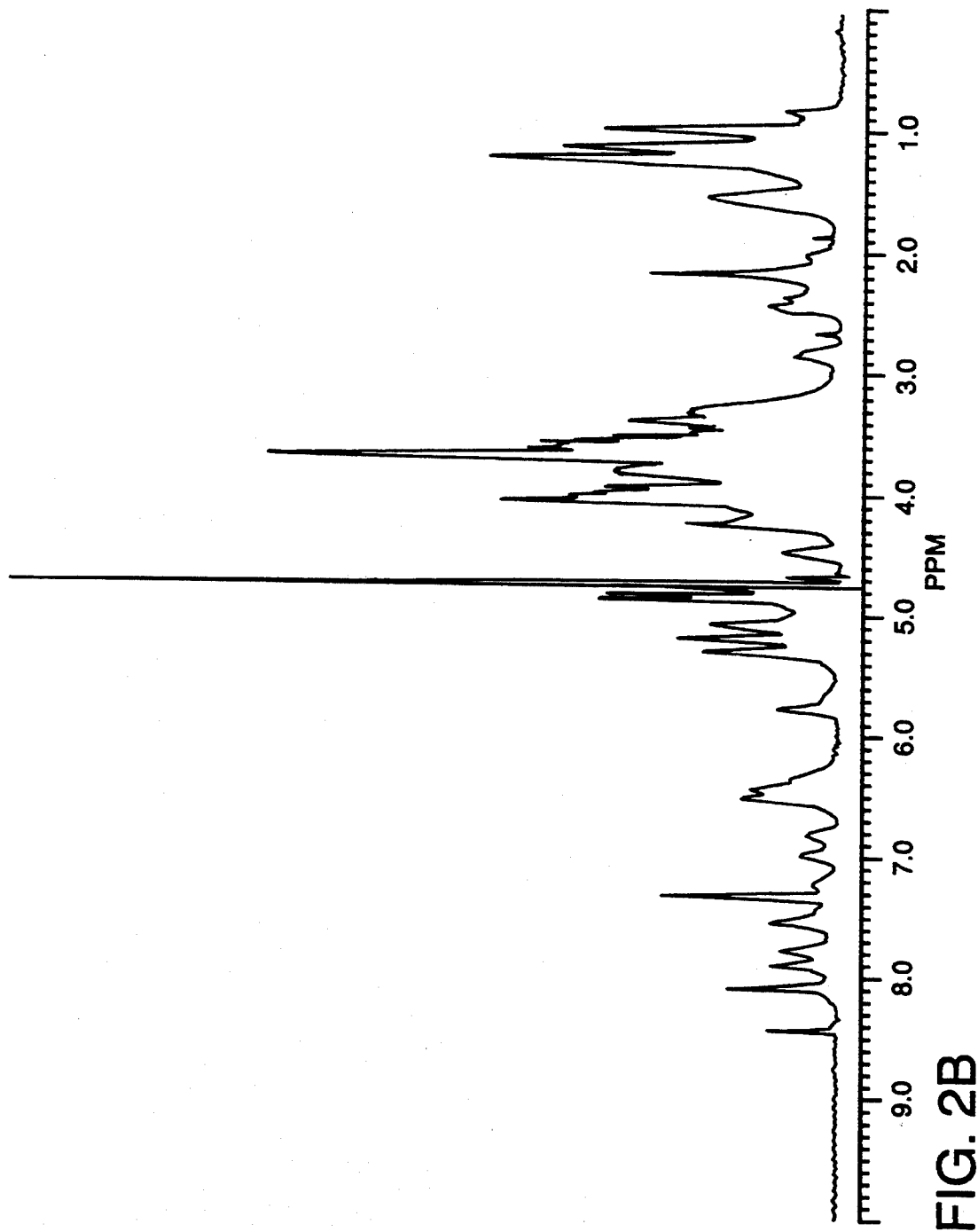

FLUORESCENT-LABELLED BLEOMYCIN ANALOGUES

This is a continuation of U.S. Ser. No. 07/881,414, filed May 11, 1992, now abandoned, which is a continuation-in-part of U.S. application Ser. No. 07/681,158, filed Apr 5, 1991, now abandoned.

BACKGROUND OF THE INVENTION

1. Field of the Invention

This invention relates to bleomycin products and the method of making and using same, and more specifically, it relates to the advantageous use of fluorescent-labelled bleomycin analogs as probes for identifying cells which are resistant or sensitive to bleomycin or bleomycin derivatives and further relates to the use of such analogs as therapeutic agents for treating malignant cells responding to bleomycin or bleomycin derivative treatment.

2. Description of the Prior Art

Antineoplastic agents are those which inhibit or prevent the growth and spread of neoplasms or malignant cells. The antineoplastic agent bleomycin (BLM) refers to a group of peptides with antitumor activity widely used in the treatment of various cancers, such as squamous cell carcinoma, testicular carcinoma and Hodgkin's disease. See, Lazo, J. S., et al., "Malignant Cell Resistance to Bleomycin Group Antibiotics," *Anticancer Drug Resistance*, pp. 267–280, (CRC Press, 1989); Carter, S. K., "Bleomycin: More Than a Decade Later," *Bleomycin Chemotherapy*, pp. 3–35, (Academic Press, Inc., 1985).

The cellular determinants responsible for regulating the toxicity of BLM remain unclear. However, the primary target for the therapeutic action of the BLM class of compounds is thought to be nuclear DNA. See Umezawa, H., "Advances in Bleomycin Studies,", *Bleomycin: Chemical, Biochemical and Biological Aspects*, pp. 24–36, (Springer-Verlag, 1979); Lazo, J. S., et al., "Initial Single-strand DNA Damage and Cellular Pharmacokinetics of BLM $A_2$," *Biochem. Pharmacol.*, 38: 2207–2213, (2989). It is believed, for example, that bleomycin causes strand scission and fragmentation of DNA and may, to a lesser extent, inhibit synthesis of RNA. Nonetheless, the magnitude of DNA cleavage and cytotoxicity do not always correlate. See Berry, D. E., et al., "DNA Damage and,Growth Inhibition in Cultured Human Cells by Bleomycin Congeners," *Biochemistry*, 24: 3207–3213, (1986); Smith, P. T. "Ferrous-iron Mediated Enhancement of DNA Damage and Recovery Potential in Bleomycin-treated Human Cells," *Biochem. Pharmacol.*, 36: 475–480, (1987).

There is also some evidence to suggest that nonnuclear lesions may also be responsible for cell death seen with BLM. For example, BLM-Fe complexes can produce lipid peroxidation in vitro and in vivo. See Lazo, J. S., et al., "*Anticancer Drug Resistance*, supra; Ciriolo, M. R., et al., "A Comparative Study of the Interactions of Bleomycin with Nuclei and Purified DNA," *J. Biol. Chem.*, 264: 1443–1449, (1989). These complexes can also produce rapid perturbations of the plasma membrane fluidity in cultured cells. See Bailly, C., et al., "Plasma Membrane Perturbations of KB3 Cells Induced by the Bleomycin-iron Complex," *Cancer Res.*, 50: 385–392, (1990). Thus, it is possible that BLM affects the plasma membrane or other organelles. See Vyskocil, F., et al., "Bleomycin Stimulates Both Membrane (Na+—K+) ATPase and Electrogenic (Na+—K+) Pump and Partially Removes the Inhibition by Vanadium Ions," *Biochem. Biophys. Res. Comm.*, 116: 783–788, (1983); Sun, I. L., et al., "Bleomycin Control of Transplasma Membrane Redox Activity and Proton Movement in HeLa Cells," *Biochem. Pharmacol.*, 34: 617–619, (1985).

In addition to the uncertain nature of the mechanisms whereby BLM affects cells, little is known about cellular BLM uptake or the dynamics of intracellular BLM distribution, because only limited amounts of the drug appear to enter cells and current analytical methods to monitor intracellular BLM are not sufficiently sensitive. Furthermore, certain cells appear to be BLM sensitive, while others are BLM resistant, and the reasons for this are not always clear, nor is it always possible to gauge the relative degrees to which certain cells are BLM-resistant or sensitive.

To understand the mode(s) of action of BLM cytotoxicity, it is important to elucidate (a) the mechanisms by which BLM enters the cell, and (b) the cytoplasmic fate of BLM following internalization. Additionally, since alteration in BLM uptake is one mechanism by which cells become resistant to BLM, understanding the process of internalization as well as of intracellular trafficking of BLM could help further clarify the cellular basis of BLM resistance.

One means of analyzing a drug's intracellular fate is to take advantage of its intrinsic fluorescent. The intrinsic fluorescent of drugs has, in the past, been useful in defining the cellular pharmacology of anticancer agents. For example, several investigators have studied the mechanisms of cytotoxicity and cellular resistance of the anticancer agent, adriamycin, by taking advantage of its intrinsic fluorescent. See Willingham, M. C., et al., "Single Cell Analysis of Daunomycin Uptake and Efflux in Multidrug-resistant and Sensitive KB Cells: Effects of Verapamil and Other Drugs," *Cancer Res.*, 46: 5941–5946, (1986); Lane, P., et al., "Temperature Dependence Studies of Adriamycin Uptake and Cytotoxicity," *Cancer Res.*, 47: 4038–4042, (1987); Herweijer, H., et al., "A Rapid and Sensitive Flow Cytometric Method for the Detection of Multidrug-Resistant Cells," *Cytometry*, 10: 463–468, (1989).

BLM has intrinsic fluorescent but, unfortunately, studies using this property of BLM have not been informative because the intrinsic fluorescent intensity of BLM is too low to be of practical utility as a cellular probe. Detailed studies of internalization as well as cellular accumulation and localization of BLM and BLM-like compounds have also been severely limited because of difficulty in obtaining higher specific activity [$^3$H]BLM.

Another approach to investigating a drug's intracellular activity is to use fluorescent analogs of the drug. Fluorescent analogs of peptides, hormones and drugs have proved valuable alternatives to using radiolabelled species for studying the processes of cellular internalization and intracellular trafficking. See Wang, Y. L., et al., "Methods in Cell Biology," Vol. 29. San Diego, Calif.: Academic Press, Inc., (1989). Fluorescein has been conjugated to methotrexate to identify transport deficient phenotypes. See Guadray, P., et al., "Fluorescent Methotrexate Labeling and Flow Cytometric Analysis of Cells Containing Low Levels of Dihydrofolate Reductase," *J Biol. Chem.*, 261: 6285–6292, (1986); Assaraf, Y. G., et al., "Identification of Methotrexate Transport Deficiency in Mammalian Cells using Fluoresceinated Methotrexate and Flow Cytometry," *Proc. Natl. Acad. Sci.* (USA), 84: 7154–7158, (1987); Assaraf, Y. G., et al., "Characterization by Flow Cytometry of Fluorescein-methotrexate Transport in Chinese Hamster Ovary Cells," *Cytometry*, 10: 50–55, (1989).

The cellular uptake and targets of estramustine have been probed using a dansylated derivative. See Sterns, M. E., et al., "Dansylated Estramustine, a Fluorescent Probe for Studies of Estramustine Uptake and Identification of Intracellular Targets," *Proc. Natl. Acad. Sci.*, (USA), 82:8483–8487, (1985).

Fluorescein isothiocyanate (FITC) has been successfully conjugated to various pharmacological agents such as methotrexate and testosterone. See Gapski, G. R., et al., "Synthesis of a Fluorescent Derivative of Amethopterin," *J. Med. Chem.*, 18: 526–528, (1975); Evarian, C., et al., "The Preparation of Three Fluorescent-labelled Derivatives of Testosterone," *Steroids*, 35: 610–619, (1980).

However, fluorescent-labelled bleomycin and bleomycin derivatives have not, to the inventors' knowledge, heretofore been identified. Accordingly, there is a need in the art to synthesize a new BLM analog that possesses enhanced fluorescent properties and which enables characterizing the biological properties of BLM and BLM analogs in vitro and in vivo, as well as in cultured BLM-sensitive and BLM-resistant cells.

SUMMARY OF THE INVENTION

The present invention has produced a solution to the above described need by providing novel highly fluorescent-labelled analogs of bleomycin and fluorescent-labelled analogs of bleomycin deriatives, which act as fluorescent probes, for detecting the intracellular uptake and distribution of bleomycin and bleomycin derivatives, having up to 300–400 times greater fluorescent than that inherent in bleomycin and bleomycin derivatives, and further are as effective and in certain cases more effective, than bleomycin and bleomycin derivatives in cleaving DNA. More specifically, a fluorescent-labelled bleomycin analog has been created, comprising a covalently linked product of bleomycin or a bleomycin derivative and a fluorescent moiety, the fluorescent moiety being present in the product in a quantity of at least one molecule of the fluorescent moiety per molecule of the bleomycin or bleomycin derivative. In a preferred embodiment of the invention, the bleomycin or bleomycin derivative has a terminal amino group and the fluorescent moiety is primarily linked to the terminal amino group. In a most preferred embodiment of the invention, the product comprises fluoromycin, or FLM, a covalently linked product of the bleomycin derivative talisomycin $S_{10b}$, (TLM $S_{10b}$) and a florescent moiety, preferably fluorescein.

In a preferred new method of using the fluorescent-labelled bleomycin or bleomycin derivative of the invention, this product is used as a probe by exposing isolated cells to the product and measuring the cell-associated fluorescent of the exposed cells with fluorescent measuring means. In this way, the relative tendency of various types of cells to be bleomycin-resistant or bleomycin-sensitive can be determined.

In yet another preferred new method of using the invention, the fluorescent-labelled bleomycin or bleomycin-derivative is used for treating cells by exposing the product of the invention to the cells, which leads to death of the exposed cells. It is believed that the new fluorescent-labelled bleomycin or bleomycin derivatives of the invention cleave DNA within the cells and this kills the cells. This method may be performed in vivo through intraveneous, intramuscular, or subcutaneous administration of the fluorescent-labelled bleomycin analog to the patient.

In another preferred embodiment of the invention, a novel method for producing the fluorescent-labelled bleomycin analog is employed. According to this method, the fluorescent-labelled bleomycin analog is prepared by forming a metal complex of bleomycin or bleomycin derivative, followed by combining a fluorescent moiety with the metal complex so formed.

It is an object of the present invention to provide a fluorescent-labelled bleomycin analog which may be used as a cellular probe of bleomycin content.

It is yet another object of the invention to provide a fluorescent-labelled bleomycin analog which may be used to cleave DNA.

It is a further object of the invention to provide a method of making fluorescent-labelled bleomycin analogs.

It is still another object of the invention to provide a method of using fluorescent-labelled bleomycin analogs to determine the relative bleomycin/bleomycin derivative resistance or sensitivity of various types of cells, most preferably, malignant cells.

It is yet another object of the invention to provide a method of using fluorescent-labelled bleomycin analogs to cleave DNA.

It is still a further object of the invention to provide a new compound which inhibits cancerous cell growth and may be used to treat tumors in patients.

These and other objects of the invention will be fully understood from the following description of the presently preferred embodiments of the invention and with further reference to the illustrations, figures and examples included herein.

BRIEF DESCRIPTION OF THE DRAWINGS

FIG. 2B is a $^1H$ NMR spectrum of Zn (II)—FLM in $D_2O$.

DETAILED DESCRIPTION OF THE PREFERRED EMBODIMENTS

Figure 1A:
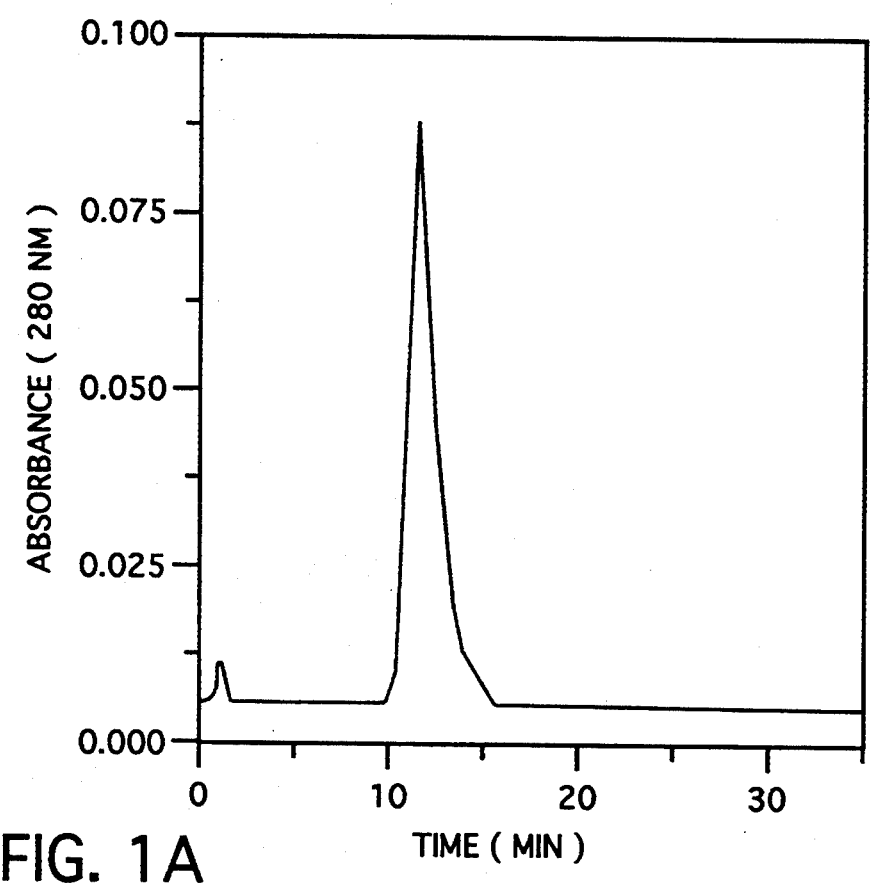
FIG. 1A is a schematic representation of the fast protein liquid chromatography of the FLM product of the present invention, demonstrating the purity of the compound.

As used herein, in the absence of a clear, express indication to the contrary at a specific location, the term "BLM" means bleomycin; "DMSO" means dimethyl sulfoxide; "EDTA" means ethylene-diaminetetraacetic acid; "FBS" means fetal bovine serum; "FITC" means fluorescein isothiocyanate; "FLM" means fluoromycin, a fluorescent-labelled derivative of talisomycin $S_{10b}$; "FPLC" means fast protein liquid chromatography; "$IC_{50}$" means concentration of drug which inhibits cell growth to 50% of control; "LBM" means liblomycin; "MTT" means 3-(4,5-dimethyl-thiazol-2-yl)-2,5diphenyltetrazolium bromide; "NMR" means nuclear magnetic resonance; "TLC" means thin-layer chromatography; "TLM $S_{10b}$" means talisomycin $S_{10b}$.

Also as used herein, absent a clear, express indication to the contrary at a specific location, the term "patient" shall mean members of the animal kingdom, including humans, regardless of whether they are at a particular time suffering from an ailment, being subjected to a diagnostic procedure or otherwise receiving medical treatment.

Knowledge of the processes of cellular accumulation and localization of DNA-interactive antineoplastic drugs, such as bleomycin (BLM), is important to understanding their mechanisms of cytotoxicity and tumor resistance. Therefore, a new compound has been synthesized, referred to herein as "fluoromycin" (FLM), a novel fluorescein-labelled derivative of talisomycin $S_{10b}$. This new compound has proven to be effective as a probe for studying cellular accumulation in BLM-sensitive and BLM-resistant cell lines. The fluorescent intensity of FLM is 300 to 400 times greater than that of BLM $A_2$, TLM S10b or the lipophilic BLM analog, liblomycin. FLM possesses an antiproliferative potency similar to liblomycin in BLM-sensitive human A-253 squamous carcinoma cells but is less potent than BLM $A_2$ or TLM $S_{10b}$. C-10E cells, a clone of A-253 cells with 40- to 50-fold resistance to BLM $A_2$ and TLM $S_{10b}$, are 50-fold resistant to FLM. A revertant cell population (C-$10E^R$) regains sensitivity to BLM $A_2$, TLM $S_{10b}$ and FLM. Flow cytometric analysis of FLM content in C-10E and C-$10E^R$ cell lines shows 4-fold and 2-fold lower fluorescent intensity, respectively, compared to A-253 cells.

Similarly, when cell-associated fluorescent is measured in A-253, C-10E and C-$10E^R$ cells by fluorescent spectrophotometry, C-10E cells are found to contain 2-fold lower levels of FLM whereas the C-$10E^R$ cells possess intermediate levels of FLM.

FLM, like BLM, also cleaves pGEM-3Z plasmid DNA in vitro in a concentration-dependent manner. These results, illustrated in greater detail in the examples, descriptions and figures presented herein, establish that FLM emulates classical BLM-like compounds and, therefore, is useful in studying the intracellular fate of BLM-like drugs as well as providing a tool to detect and isolate BLM-resistant and BLM-sensitive cells. Indeed, FLM may itself be used as an antineoplastic agent.

Compound (1) below is a schematic representation of the structure of a bleomycin compound. As seen in the illustration, the compound contains at the distal end of the molecule an "R" group which is generally an amine. This "R" group is known as the "terminal amine."

For purposes of the present invention, R of compound (1) may be OH, (Bleomycinic Acid); NH—$(CH_2)_3$—S—$CH_3$ (Dimethyl Bleomycin $A_2$); NH—$(CH_2)_3$—$NH_2$ (Bleomycin $A'_2$); or NH—$(CH_2)_3$—NH—$(CH_2)_4$—$NH_2$ (Bleomycin $A_5$).

BLEOMYCIN

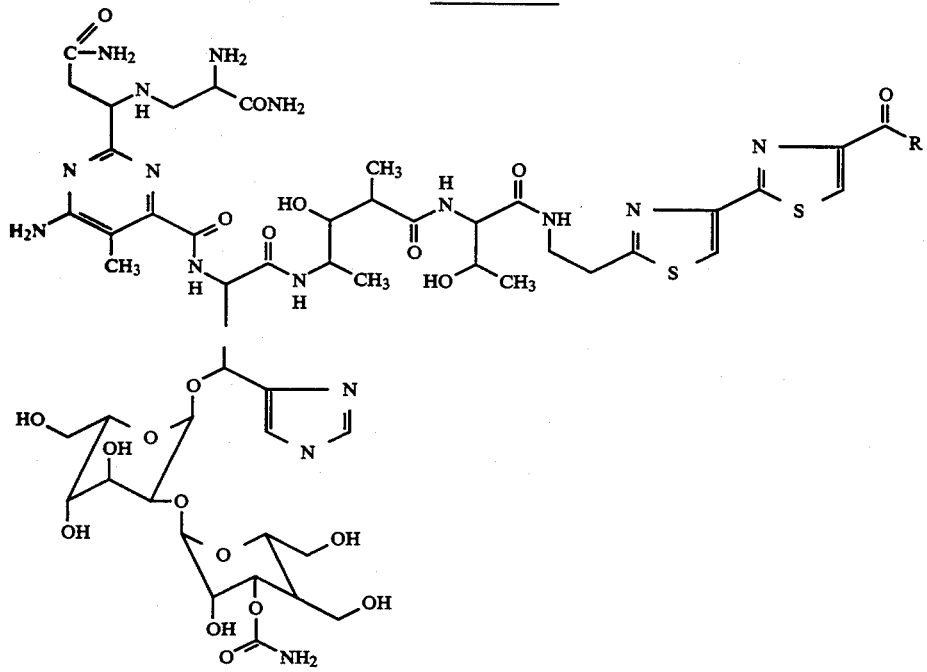

(1)

Compound (2) below is a schematic representation of a talisomycin compound, which differs from the bleomycin of compound (1) primarily in the placement of a talose sugar group about midway along the molecule's backbone. For purposes of the present invention, the R group of compound (2) may be NH—$(CH_2$-

)$_3$—CH(NH$_2$)—CH$_2$—CO—NH—(CH$_2$)$_3$—NH—(CH$_2$)$_4$—NH$_2$ (Talisomycin A); NH—(CH$_2$)$_3$—NH—(CH$_2$)$_4$—NH$_2$ (Talisomycin B); or NH—(CH$_2$)$_4$—NH$_2$ (Talisomycin S$_{10b}$).

We have found that by first forming a metal complex of the TLM S$_{10b}$ molecule of compound (2) and then combining the metal-complexed TLM S$_{10b}$ with a fluorescent moiety, such as fluorescein, illustrated as compound (3) below, a new compound, such as fluoromycin, illustrated as compound (4) below, is produced.

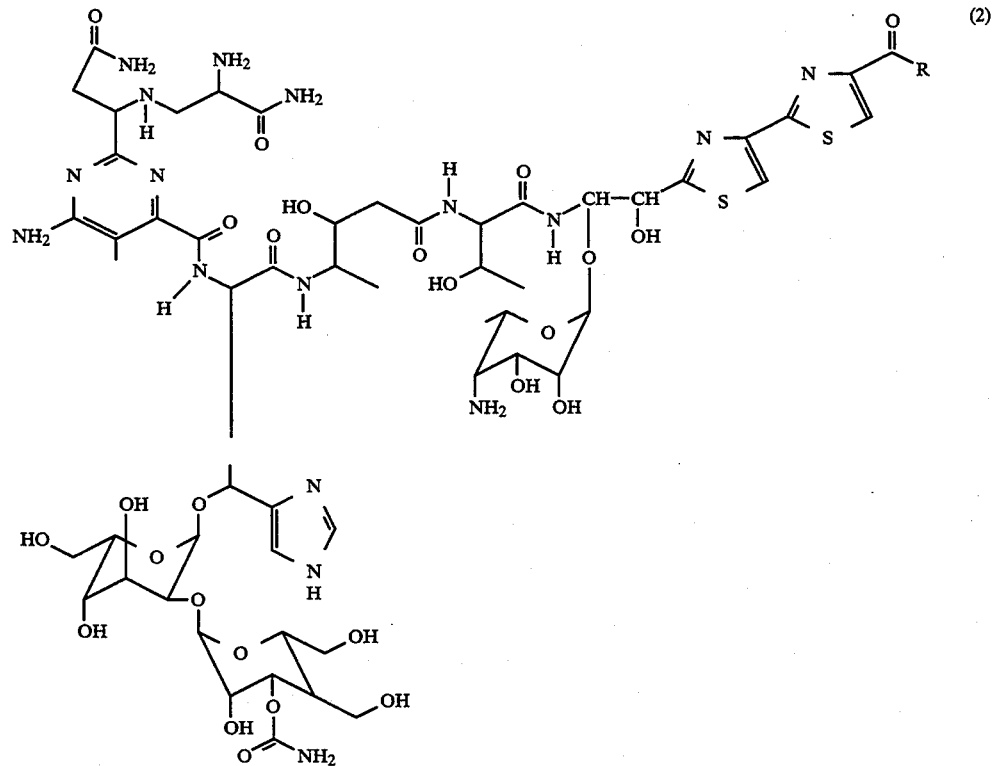

Talisomycin (2)

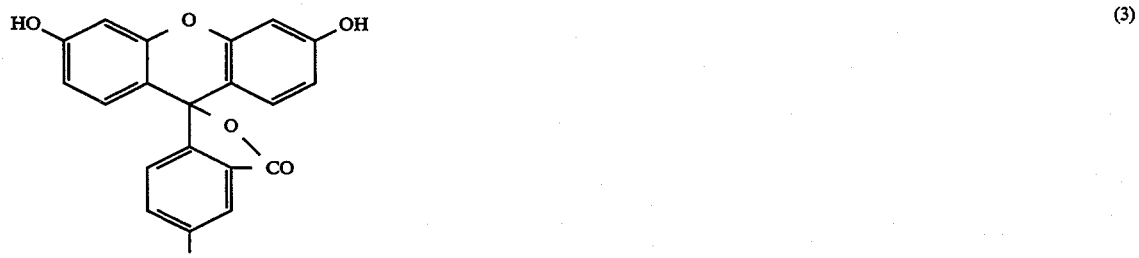

FLUORESCEIN (3)

FLUOROMYCIN

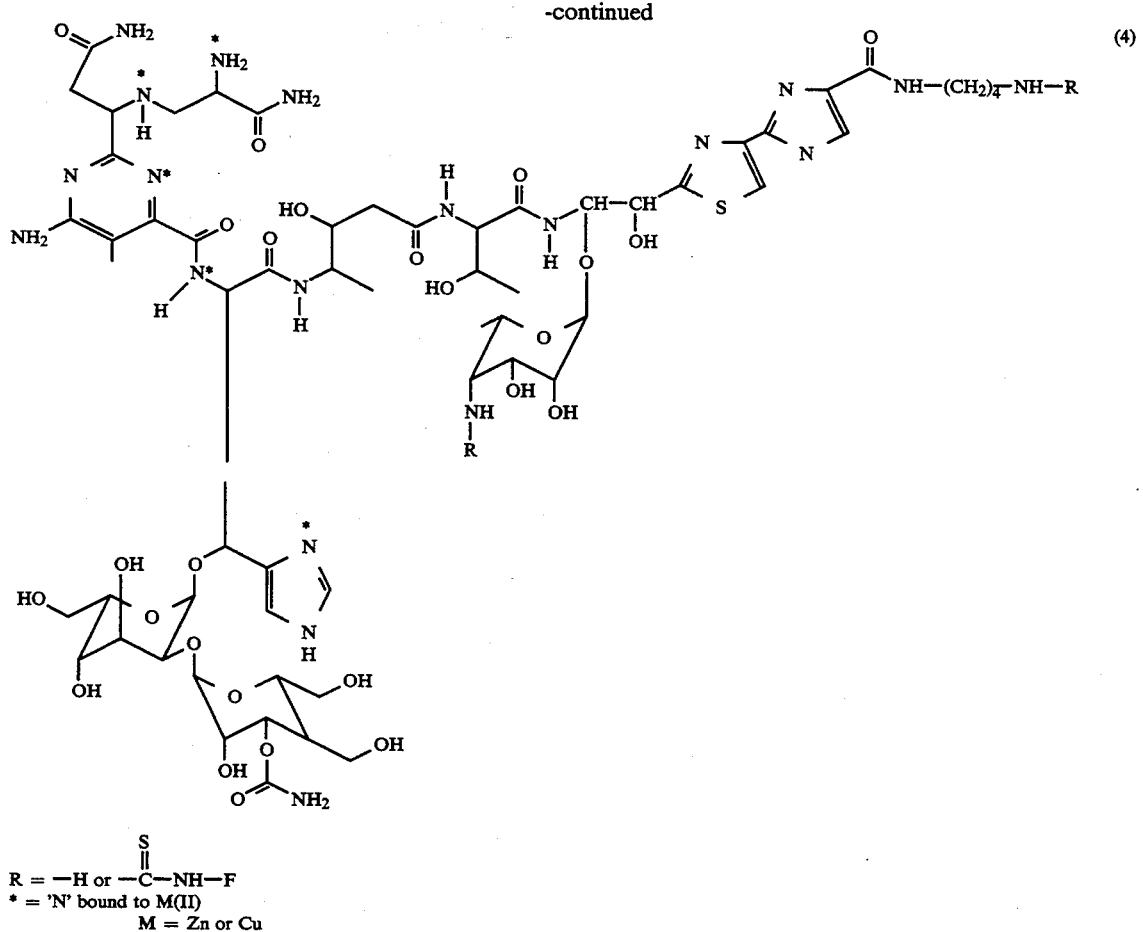

R = —H or —C(=S)—NH—F
* = 'N' bound to M(II)
M = Zn or Cu

In this compound (4), the "R" groups are either —H or —C=S—NH—F where F is fluorescein or some other fluorescent moiety. While, according to the present invention, both "R" groups of compound (4) may become fluorescent-labelled, it is preferred that only the terminal amine "R" group becomes so labelled. While only one "F" moiety is shown being attached to the terminal amine of compound (4), it is contemplated that the present invention includes a plurality, preferably from one to five, fluorescent moieties being attached to the bleomycin or bleomycin analog, preferably at the terminal amine. As used herein, the term "fluorescent-labelled analog" is not intended to include bleomycin or bleomycin derivatives which have some inherent fluorescent but have not been combined with a fluorescent moiety as described herein.

The fluorescent-labelled analogs of bleomycin or bleomycin derivatives, such as FLM, are prepared in the following manner. First, a bleomycin or bleomycin derivative for which cellular activity characterization is desired is selected. Any bleomycin or bleomycin derivative may be used, provided it has a reactive moiety to which a fluorescent label can be attached.

These bleomycin or bleomycin derivatives can be isolated from streptomyces verticillus, see Umezawa H., et al., *Journal of Antibiotics*, Ser. A., Vol. XIX p. 200–215 (1966), incorporated by reference herein, or can be synthesized as described by Aoyagi, et al., *J. Am-Chem. Soc.* 104: 5537–5538 (1982), incorporated by reference herein.

It is preferred to first form a metal complex of the bleomycin or bleomycin analog to be fluorescent-labelled. This is especially true when the bleomycin analog comprises, for example, TLM $S_{10b}$, which has, in addition to a terminal amino group, amino groups residing in the DNA-damaging domain of the molecule, that is, distal from the terminal amine. It is preferred that these non-terminal amino groups not be fluorescent-labelled, as this would interfere too greatly with the antineoplastic properties of the resulting analog. Forming a metal complex protects these non-terminal amino groups, labelled with an * as illustrated in compound (4), from being fluorescent-labelled, and frees the terminal amine of the bleomycin molecule to react with the fluorescent moiety being used.

Preferably, the bleomycin or bleomycin derivative is metal complexed with a +2 valence metal, such as zinc or copper. However, other metals, such as Co and Cd could also be used to form the metal complex. The metal complex is preferably formed using a metal salt, such as $ZnCl_2$, $CuCl_2$, $CdCl_2$, $CoCl_2$, $ZnSO_4$, $CdSO_4$, and $CuSO_4$, which is dissolved in a solution, preferably an aqueous solution into which the bleomycin or bleomycin derivative is dissolved. A metal complex forms under ambient conditions and the reaction proceeds to completion within about one minute. The amount of metal used, of course, depends upon the amount of bleomycin or bleomycin derivative being metal-complexed.

After the metal complex has formed, as indicated by a color change, for example, by the formation of a blue color when $CuCl_2$ or $CuSO_4$ is used, the solution containing the metal complex is buffered and the pH adjusted to about 8.5–9.5, preferably pH 9.0. Any suitable buffers and pH adjustment agents may be used, and bicarbonate buffer and solid sodium carbonate for pH adjustment have proven effective. Phosphate or borate buffers can also be used.

Following buffering/pH adjustment, a fluorescent moiety is added to the metal complex-containing solution. This addition step preferably takes place in the absence of ambient light. Various fluorescent moieties may be used, including by way of example but not limitation, fluorescein (FITC, bromomethyl fluorescein, 5- or 6-iodoacetamidofluorescein, 4'- (((iodoacetyl) amino) methyl) fluorescein and 4'-5'-di (((iodoacetyl) amino) methyl) fluorescein), as well as 4-halo-7-nitrobenzo-2-oxa-1, 3, diazole (NBD), NBD halides,4,4-difluoro-5,7-dimethyl-4-bora-3a,4a-diaza-S-indacene-3-propionic acid (BODIPY), tetramethylrhodamine, pyrenes and cyanine dyes (e.g. CY5.13 or CY5.18). The fluorescein may be obtained from fluorescein isothiocyanate or succinimidyl ester, bromomethyl fluorescein, and 5- or 6-iodoacetamidofluorescein; NBD may be obtained from NBD-fluoride or NBD-chloride; BODIPY, may be obtained from BODIPY isothiocyanate or BODIPY halide; pyrene may be obtained from pyrene carboxaldehyde or pyrene alkyl halides; tetramethylrhodamine may be obtained from tetramethylrhodamine isothiocyanate or succinimidyl ester or tetramethylrhodamine alkyl halides and cyanine may be obtained from cyanine isothiocyanate or iodoacetamido cyanine dyes.

It is preferred that the fluorescent moiety be one which significantly increases the fluorescent of the resulting fluorescent-labelled analog, and further be preferentially covalently linked to the terminal amine and most preferably be covalently linked to only the terminal amine of the bleomycin or bleomycin analog being fluorescent-labelled.

The covalent linkage of fluorescent moiety to the metal complex-containing solution, results, with stirring at ambient conditions, after about 90 minutes, in a crude reaction product which is preferably freeze-dried to obtain a solid reaction mixture. Of course, other reaction product recovery methods well known to those skilled in the art, such as centrifuging, molecular filtering and evaporation could likewise be employed.

The recovered solid reaction mixture generally contains primarily the desired end product along with various impurities, and is preferably purified to recover the desired fluorescent-labelled product. Any known purification method may be used. Preferably, the mixture is loaded onto TLC plates which allow separation of the desired end product to occur as hereinafter discussed. Alternatively, purification may be accomplished by FPLC.

Various forms of bleomycin and bleomycin derivatives may be fluorescent-labelled according to the invention, including, by way of example but not limitation, TLM $S_{10b}$, S-dimethyl bleomycin $A_2$, bleomycinic acid, bleomycin $A_2'$ and bleomycin $A_5$.

It is, of course, possible to fluorescent-label bleomycin or bleomycin derivatives without first forming a metal complex. However, this presents a greater risk of fluorescent-labelling amine groups in the active region of the bleomycin or bleomycin analog molecule. The method of fluorescent-labelling non-metal-complexed-bleomycin or bleomycin derivatives is the same as described above, except the metal-complex forming step is eliminated.

The fluorescent-labelled analogs of bleomycin and bleomycin derivatives of the invention have proven useful in a variety of applications. In a most preferred method of the invention, a fluorescent-labelled analog is used to determine vicariously the expected uptake of the corresponding bleomycin or bleomycin derivative in cells.

A preferred method comprises incubating cells being studied, in vitro, with a fluorescent-labelled analog of BLM or BLM derivative for a sufficient time period to allow for cellular uptake of the fluorescent-labelled BLM or BLM derivative. This time period varies, of course, depending upon the type of cell being studied and type of fluorescent probe being used. However, generally an incubation period of at least about 60 minutes has proven adequate.

After the cells have been incubated, their fluorescent is measured. The BLM or BLM derivative sensitivity or resistance with respect to these cells can in this way be measured by measuring the degree of fluorescent of the exposed cells. This may be done, for example, by calibrating the known rate of cellular drug uptake or the amount of cellular fluorescent at a given time with known fluorescent values for a particular cell type using the particular BLM or BLM derivative, and comparing the relative fluorescent of the cell type being studied using the same fluorescent analog of that BLM or BLM derivative. Alternatively, a comparison of relative fluorescent between different cell types using the same fluorescent-labelled analog may be made or a comparison of same cell types sensitivity to different fluorescent-labelled analogs may be measured.

The cells being evaluated may be obtained from commercial sources or from a patient, e.g., a biopsy. When the cells are taken from a patient, the fluorescent-labelled analog may first be administered therapeutically as hereinafter discussed, and, after sufficient time has elapsed to allow for cellular uptake in vivo, a biopsy may be taken of the tumor or other areas of cellular interest. Alternatively, a biopsy may be taken first, and the recovered cells treated with the fluorescent-labelled analog in vitro, as previously discussed.

Yet another method of the invention involves using fluorescent-labelled analogs of BLM or BLM derivatives to cleave DNA. Specifically, these analogs are employed, preferably in the presence of Fe(II) (from $FeSO_4$), to cause single and double strand DNA breaks.

According to this method, the fluorescent-labelled analog of BLM or BLM derivative is exposed, in the presence of Fe(II), in vitro to DNA from cells under diagnostic study. More particularly, stoichiometric amounts of fluorescent-labelled analog, such as FLM, and Fe(II) are incubated for about 1–30 minutes with the DNA under study, to determine the rate of DNA cleavage and the potency of the particular analog with respect to the particular DNA being studied. Concentration ranges from about 0.01–200 $\mu$molar for this method, which may be used on a wide variety of DNA, including form I, II and III plasmid DNA, as well as eukaryotic DNA, prokaryotic DNA and viral DNA. Such analytical methods can be used to compare relative rates of DNA cleavage and relative potency of BLM or BLM derivatives.

Another preferred method of the invention involves inhibiting cell growth, such as cancerous cell growth, by exposing cells in vivo or in vitro to an effective dosage of a fluorescent-labelled analog of bleomycin or a bleomycin derivative. The cells may be from the group carcinomas, melanomas, lymphomas, sarcomas and leukemias. More specifically, squamous cell carcinomas, testicular carcinomas, non-Hodgkins and Hodgkins lymphomas can be treated.

The fluorescent-labelled analog, which may be FLM, for example, is administered in a dosage of about 0.001 to 3 mg/kg daily, weekly, biweekly or monthly, in the case of in vivo treatment on a human subject and in a concentration of about $10^{-9}$ to $10^{-4}$M in the case of in vitro analysis. Preferably, for in vitro analysis, the sample being studied for cell growth inhibition is incubated at a temperature of about 37° C. for about 96 hours.

When a fluorescent-labelled analog of BLM or BLM derivative is used therapeutically on a patient, it is preferably administered intravenously, intramuscularly or subcutaneously. The transport agent is preferably an aqueous solution used in concentrations and with additives as used in the administration of bleomycin and bleomycin derivates and known to those skilled in the art.

In order to verify the concepts of the invention a series of experiments have been performed. The following materials were used in the following experiments.

TLM $S_{10b}$ and BLENOXANE ® were supplied by Bristol Myers Squibb Co. (Wallingford, Conn.). BLM $A_2$ was isolated from BLENOXANE ® by a previously described FPLC method. See, Mistry, J. S., et al., "Separation of Bleomycins and their Deamido Metabolites by High Performance Cation-exchange Chromatography," *J. Chromat;* 514:86–90 (1990), incorporated by reference herein. Liblomycin (LBM) was acquired from Nippon Kayaku Co. Ltd. (Tokyo, Japan); FITC was obtained from Molecular Probes, Inc. (Eugene, OR); dithizone was from Mallinckrodt, Inc. (Paris, Kentucky). Analytical TLC plates: Silica Gel 60 $F_{254}$ (5×20 cm; layer thickness, 0.2 mm) precoated plates were from E. Merck (Darmstadt, Germany) and reverse phase, hydrocarbon impregnated, prescored RPS-F (10×20 cm; layer thickness, 0.25 mm) precoated plates were from Analtech, Inc. (Newark, Del.). Preparative reverse phase, hydrocarbon impregnated (20×20 cm; layer thickness, 0.5 mm) plates were also obtained from Analtech, Inc. Mono S HR 5/5 cation-exchange column (5 cm×5 mm I.D., 10 μm particle size, 25000 theoretical plates/m) was obtained from Pharmacia LKB Biotechnology (Piscataway, N.J.). MTT and DMSO were obtained from Sigma Chemical Co. (St. Louis, Mo.); pGEM-3Z plasmid DNA was obtained from Promega (Madison, Wis.). All other chemicals and solvents were acquired from either Fisher Scientific Co. (Pittsburgh, Pa.) or Aldrich Chemical Co. (Milwaukee, Wis.).

The reaction of FITC with TLM S10b was monitored by using silica gel 60 $F_{254}$ TLC plates (1:1 MeOH:10% NH$_4$OCOCH$_3$ as a solvent system) or reverse-phase, hydrocarbon-impregnated TLC plates (40:60 MeOH:H$_2$O as a solvent system). FLM was isolated as a major product from unreacted starting materials and two other minor products by using preparative reverse phase TLC plates and MeOH:H$_2$O (40:60) as a solvent system. TLC spots were visualized under short and long wavelength UV light.

Absorption spectra were obtained using a Perkin-Elmer (Lambda 2) UV/VIS spectrophotometer. Fluorescence spectra were obtained by using either a Perkin-Elmer 650-10S fluorescent spectrophotometer or a SPEX Fluorolog 2. Proton NMR spectra were recorded with a Bruker 300 MHz pulsed fourier transform spectrometer. The chemical shifts were determined with respect to internal standards: tetramethylsilane or 4-trimethylsilylpropanesulfonic acid.

Example 1

Chemical Synthesis and Analysis of Fluorescent-labelled Bleomycin Derivative A zinc complex of TLM S10b was first prepared by dissolving 15 mg (9.7 mmol) TLM $S_{10b}$ in 0.5 ml H$_2$O containing 1.47 mg (10.7 mmol) ZnCl$_2$. Bicarbonate buffer (2.5 ml, 50 mM, pH=9.0) was then added to the Zn(II)—TLM $S_{10b}$ complex and pH was adjusted to 9.0 with solid sodium carbonate. FITC (3.9 mg, 10 mmol) dissolved in bicarbonate buffer (3 ml) was then added dropwise to the Zn(II)—TLM $S_{10b}$ complex over a period of 20 minutes. The solution was stirred at room temperature in the dark for 90 minutes, then the crude reaction-mixture was lyophilized to obtain an orange solid. The orange solid was dissolved in 1.5 ml H$_2$O, divided into two equal volumes and loaded on two separate preparative TLC plates. The plates were allowed to develop in the dark for 3 hours using MeOH:H$_2$O (40:60) as the solvent system. A major band corresponding to Zn(II)—FLM ($R_f$=0.32) was scraped off the plates and extracted in the dark, with 5×15 ml H$_2$O:EtOH (1:1) mixture. EtOH was removed with a rotary evaporator under reduced pressure; and the aqueous solution was lyophilized to obtain pure Zn(II)—FLM with a 72% yield. Similarly, Cu(II)—FLM was synthesized.

In order to protect the amino groups of TLM $S_{10b}$ residing in the metal binding/DNA damaging domain, a 1:1 Zn(II)—TLM $S_{10b}$ complex of TLM $S_{10b}$ was first prepared. The primary amino group on the C-terminal moiety of TLM $S_{10b}$ was thus free to react with FITC, although some reactivity of FITC with the sterically hindered —NH$_2$ group of talose sugar would be predicted. After reacting FITC with Zn(II)—TLM $S_{10b}$ at pH 9.0, FLM and two other minor products ($R_f$=0.46 and 0.9) were isolated by reverse phase preparative TLC. The purity of FLM was confirmed by its migration as a single spot on 2 different TLC systems (reverse phase, $R_f$=0.32 and silica gel, $R_f$=0.72 with the solvent systems described herein) as well as by FPLC. FIG. 1A shows the Mono S FPLC profile of purified FLM. FLM eluted off this column as a single peak with a retention time of 11.5 minutes.

Figure 1B:
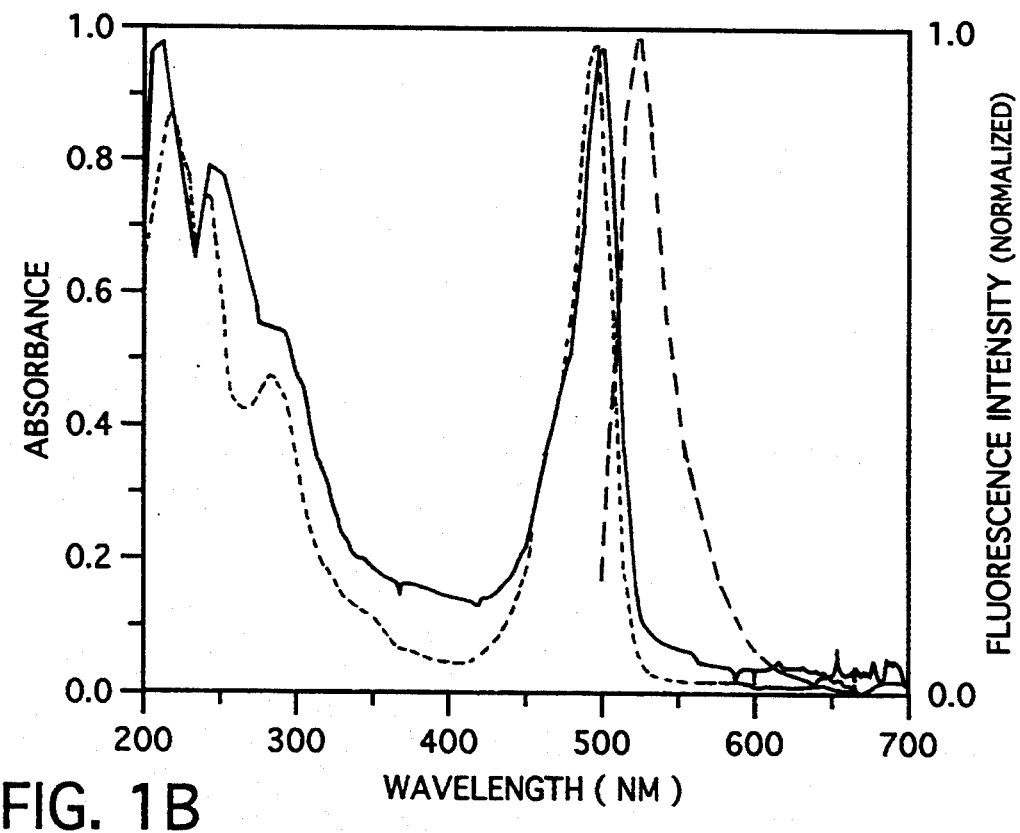
FIG. 1B is a comparative absorption and fluorescent spectrum of the FLM compound of the present invention as compared to an absorbance spectrum for a 1:1 mixture of the components used to synthesize FLM.

FIG. 1B compares the absorption spectrum of a mixture containing one equivalent Zn(II)—TLM $S_{10b}$+ one equivalent fluorescein (........), with that of FLM (a covalently linked product of TLM $S_{10b}$ and FITC) (—). The absorption spectrum of FLM was a composite of the chromophoric groups present in TLM $S_{10b}$ and FITC. Its most prominent features were the characteristic pyrimidine and bithiazole absorbances of TLM $S_{10b}$ at 245 and 292 nm, respectively, and the prominent fluorescein peak at 497 nm with a molar extinction coefficient of 45,000. A comparison of $A_{497}/A_{292}$ ratio of the 1:1 mixture of fluorescein and TLM $S_{10b}$ with that of $A_{497}/A_{292}$ ratio of FLM showed that the two ratios were approximately the same, suggesting that FLM was a conjugate that contained one molecule of fluorescein per molecule of TLM $S_{10b}$. Similarly, when the absorption spectra of the other two minor products were compared with that of the mixture containing one equivalent Zn(II)—TLM $S_{10b}$+ one equivalent fluorescein, it was found that one product ($R_f$=0.46) was a conjugate containing one molecule of fluorescein per molecule of TLM $S_{10b}$ whereas the other product ($R_f$=0.9) was a conjugate containing two molecules of fluorescein per molecule of TLM $S_{10b}$.

FIG. 1B also shows the fluorescent emission spectrum (- - -) of FLM. Thus, a solution of FLM in 50 mM bicarbonate buffer (pH=9.0) when excited at 497 nm, displayed a fluorescent emission maximum at 523 nm with a quantum yield of 0.71. When fluorescent intensities of equimolar solutions of BLM $A_2$, TLM $S_{10b}$ and LBM were compared with that of FLM, it was found that fluorescent intensity of FLM was 300 to 400 times greater than that of the other three agents. For example, the relative fluorescent units for 1 $\mu$M solutions of FLM, TLM $S_{10b}$, BLM $A_2$ and LBM were 836, 2.6, 2.7 and 2.1, respectively.

Figure 2A:
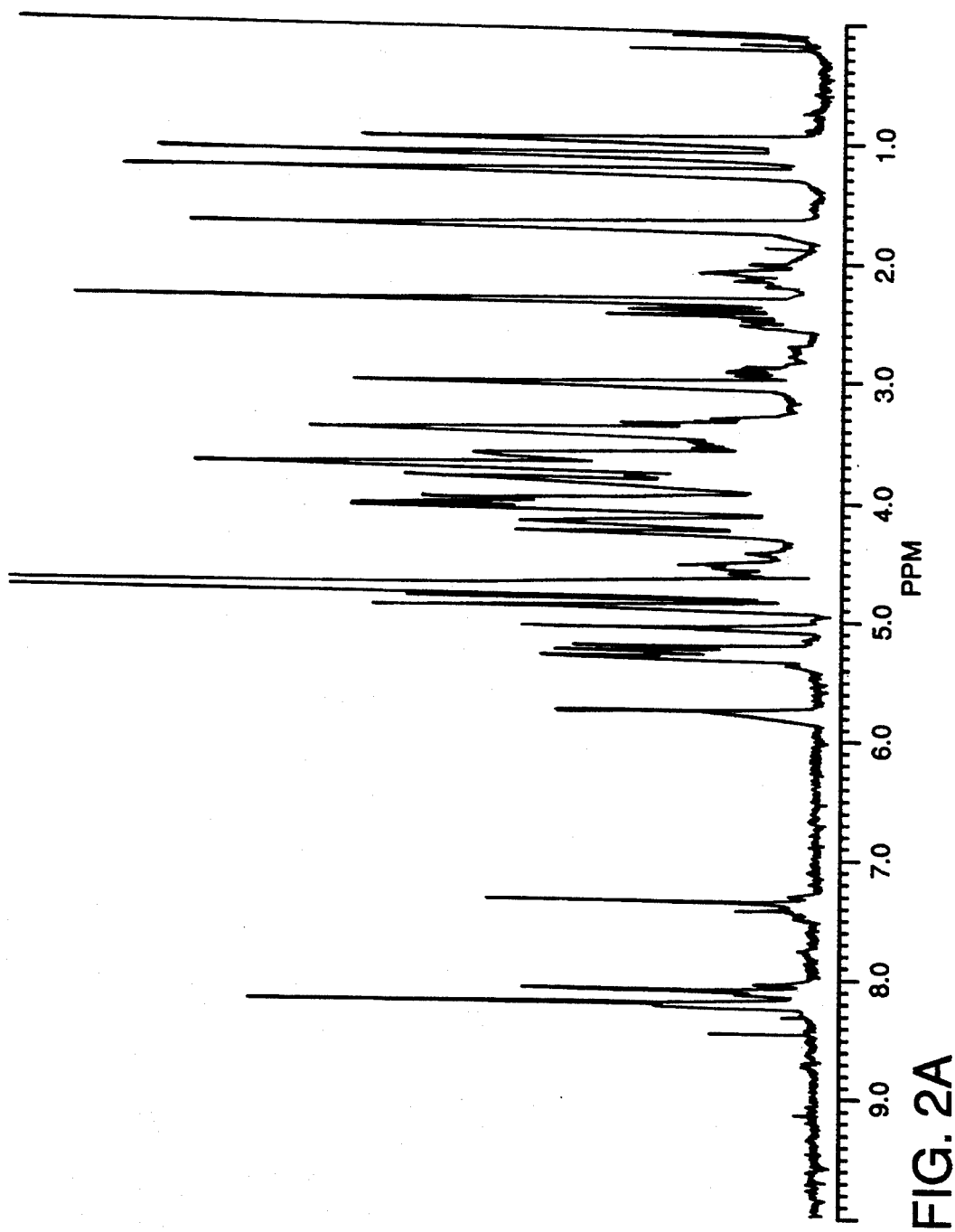
FIG. 2A is a $^1H$ NMR spectrum of Zn (II)—TLM $S_{10b}$ in $D_2O$.

FIG. 2A illustrates the $^1$H NMR spectrum of Zn(II)—TLM $S_{10b}$. The presence of methyl, methylene and methine proton resonances of TLM $S_{10b}$ is evident from the signals between 0.0–6.0 ppm whereas the signals at 7.4 (1H, imidazole), 8.1 (1H, bithiazole) and 8.2 (2H, imidazole and bithiazole) ppm represent the four aromatic protons of TLM $S_{10b}$. FIG. 2B shows the $^1$H NMR spectrum of Zn(II)—FLM which displayed the characteristic methyl, methylene and methine resonances (0.0 –6.0 ppm) due to TLM $S_{10b}$ except for the methylene protons attached to the terminal primary amino group of TLM $S_{10b}$ (shown as a triplet at 3.1 ppm in FIG. 2A). The absence of this methylene proton signal at 3.1 ppm in the spectrum of FLM suggests that the FITC molecule reacted with the primary terminal amino group of TLM $S_{10b}$ so that the methylene group in FLM is now adjacent to a thiourea type linkage (instead of being adjacent to the primary amino group, as in TLM $S_{10b}$). As a result of this change in the functional groups around the methylene protons, the methylene proton signal in FLM appears to be shifted approximately 0.3 ppm downfield. Apart from the four aromatic proton resonances due to TLM $S_{10b}$ (7.4 and 8.1 ppm, 2H of imidazole; 7.8 and 7.95 ppm, 2H of bithazole), the appearance of additional proton signals in the aromatic region (6.3–8.3 ppm) confirmed the presence of fluorescein moiety in FLM. The proton integration in the aromatic region further established that only one molecule of fluorescein was covalently linked to TLM $S_{10b}$ to generate FLM.

Example 2

Antiproliferative Activity of FLM with BLM resistant or sensitive cells

A-253 human head and neck squamous carcinoma cells were obtained from the American Type Culture Collection (Rockville, Md.) and were grown in McCoy's medium supplemented with 10% fetal bovine serum (Hyclone, Logan, Utah) as previously described. See, Lazo, J. S., et al., "Characteristics of Bleomycin-resistant Phenotypes of Human Cell Sublines and Circumvention of Bleomycin Resistance by Liblomycin," Cancer Res, 49: 185–190, (1989). The BLM-resistant (C-10E) cell line was derived from A-253 cells as previously described. Id., incorporated by reference herein, and was maintained in the continuous presence of 50 nM BLM. The revertant (C-10E$^R$) cells were obtained by growing C-10E cells in the absence of BLM for 3 months. Cell lines were maintained at 37° C. in a humidified incubator with 95% air, 5% $CO_2$ atmosphere.

The effect of drugs on cellular proliferation was determined using the previously described MTT microculture assay. See, Twentyman, P. R., et al., "Study of Some Variables in a Tetrazolium Dye (MTT) Based Assay for Cell Growth and Chemosensitivity," Br. J Cancer, 56: 279–285, (1987). Exponentially growing cells were plated at a density of 2 to 4×$10^3$ cells per well in 100 $\mu$l volume into 96-well microtiter plates (Costar, Cambridge, Mass.). After 3 hours, various concentrations of drugs were added and the plates were incubated for 4 days at 37° C. under humidified 5% $CO_2$-95% air atmosphere. After 4 days, the medium was replaced with 100 $\mu$l of 1 mg/ml MTT in McCoy's medium, and cells were incubated with MTT solution in McCoy's medium for 3 hours at 37° C. Excess MTT was removed, the formazan generated was dissolved in 100 $\mu$l DMSO, and the absorbance at wavelength 540 nm was determined spectrophotometrically (Titertek Multiskan; Flow Labs, McLean, Va.). The drug concentrations required to inhibit cell growth by 50% ($IC_{50}$) were then determined.

Figure 3A:
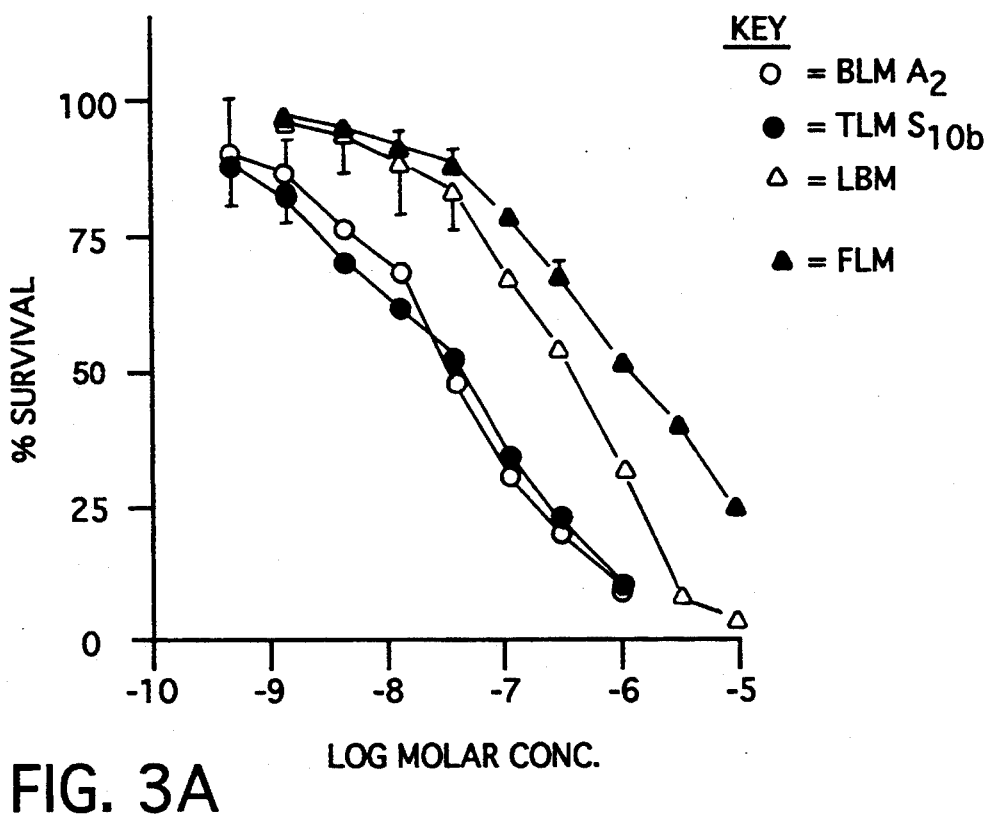
FIG. 3A is a graph illustrating the growth inhibitory effects of human A-253 cells to various concentrations of bleomycin and bleomycin analogs.

Continuous exposure of the BLM-sensitive A-253 cells to BLM $A_2$, TLM $S_{10b}$, LBM and FLM produced a concentration-dependent inhibition of growth (FIG. 3A) by all the agents tested. The concentration-response curves for BLM $A_2$ and TLM $S_{10b}$ (open and closed circles, respectively) were nearly superimposable and $IC_{50}$ values for the two drugs were found to be 37 and 50 nM, respectively. FLM (closed triangles) possessed antiproliferative potency ($IC_{50}$=1.25 $\mu$M) comparable to that of LBM (open triangles) ($IC_{50}$=0.5 $\mu$M), and was 25 and 33 times less potent than TLM $S_{10b}$ and BLM $A_2$, respectively. The other two minor products isolated from the reaction-mixture of TLM $S_{10b}$ and FITC, were also evaluated for their growth-inhibitory potency on A-253 cells and found to be inactive.

Figure 3B:
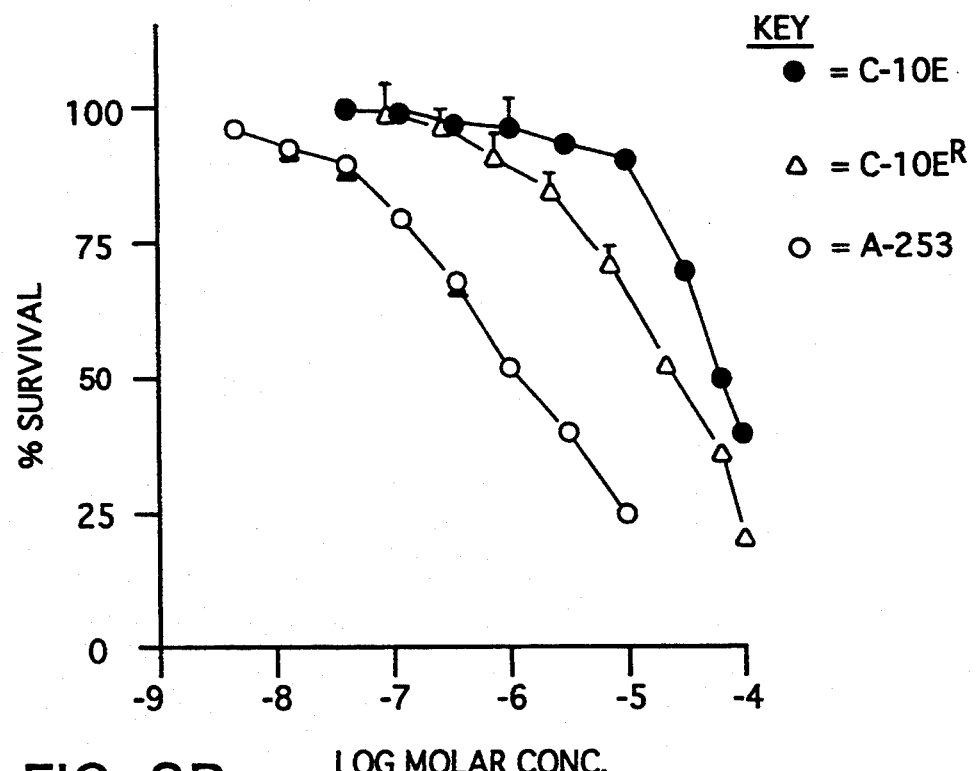
FIG. 3B is a graph illustrating comparative concentration responses of different types of cells to FLM exposure.

FIG. 3B shows that C-10E cells, which are BLM $A_2$ and TLM $S_{10b}$ resistant, are also highly resistant to FLM (closed circles), and that the revertant C-10E$^R$ cells (open triangles) possess an intermediate level of resistance to FLM. Table 1 summarizes the relative sensitivities of A-253, C-10E and C-10E$^R$ cells to the various BLM analogs. Evaluation of antiproliferative activity of FLM by growth inhibition assay indicated that FLM possesses significant growth inhibitory potency with an $IC_{50}$ value comparable to that of LBM, and 25–30 times higher than TLM $S_{10b}$ or BLM $A_2$. Interestingly, C-10E cells remain resistant to FLM but sensitive to LBM; the resistance index for FLM is comparable to that for BLM $A_2$ or TLM $S_{10b}$ and the resistance index for LBM is 1.1. Furthermore, the revertant C-10E$^R$ cells also maintain a degree of resistance to FLM similar to that for BLM $A_2$ or TLM $S_{10b}$. Thus, cytotoxicity studies and resistance profiles for this compound suggest that FLM emulates classical BLM-like compounds and that it is useful in studies of cellular phenotypes with low or high BLM accumulation.

TABLE 1

Drug sensitivities of A-253, C-10E and C-10E ® cells Cells were exposed to drugs for 4 days and inhibition of cellular proliferation was determined spectrophotometrically as described herein. Numbers ± SEM is the result of 16 or more determinations. The resistance index is indicated in parentheses below the $IC_{50}$ value and is calculated as the ratio of $IC_{50}$ for C-10E or C-10E ® cells compared to the $IC_{50}$ for A-253 cells. ND = not determined.

| | $IC_{50}$ | | |
|---|---|---|---|
| Compound | A-253 | C-10E | C-10E ® |
| BLM $A_2$ (nM) | 37 ± 1.2 | 1490 ± 33$^a$ | 480 ± 22$^a$ |

TABLE 1-continued

| | | (40) | (13) |
|---|---|---|---|
| TLM $S_{10b}$ (nM) | 50 ± 2.3 | 2700 ± 23[a] | 410 ± 9[a] |
| | | (54) | (8) |
| LBM (μM) | 0.5 ± 0.02 | 0.57 ± 0.02 | ND |
| | | (1.1) | |
| FLM (μM) | 1.25 ± 0.08 | 66 ± 1.7[a] | 22 ± 1.1[a] |
| | | (53) | (18) |

[a] $p < 0.001$ compared to A-253 cells using unpaired Student's t-test

Example 3

Use of FLM to Detect the Cellular Level of BLM-like Drug and Drug Resistance Exponentially growing A-253, C-10E or C-10E$^R$ cells were harvested and approximately $1.0 \times 10^6$ cells were incubated for 60 minutes at 37° C. with 100 μM FLM in 200 μl medium. For each analysis, a "control" was included in which each cell line was incubated under identical conditions in the absence of FLM. Drug incubation was terminated by washing the cells with $3 \times 1$ ml of ice-cold PBS. Cells were then suspended in 100 μl PBS, fixed with 2% paraformaldehyde in 100 μl PBS and analyzed by flow cytometry using a Becton-Dickinson FAC Star. Analysis was done using a 2 W laser tuned in at 488 nm at an output strength of 200 mW. The band pass filter range =530/30. The total number of cells analyzed was 5,000.

Figure 4:
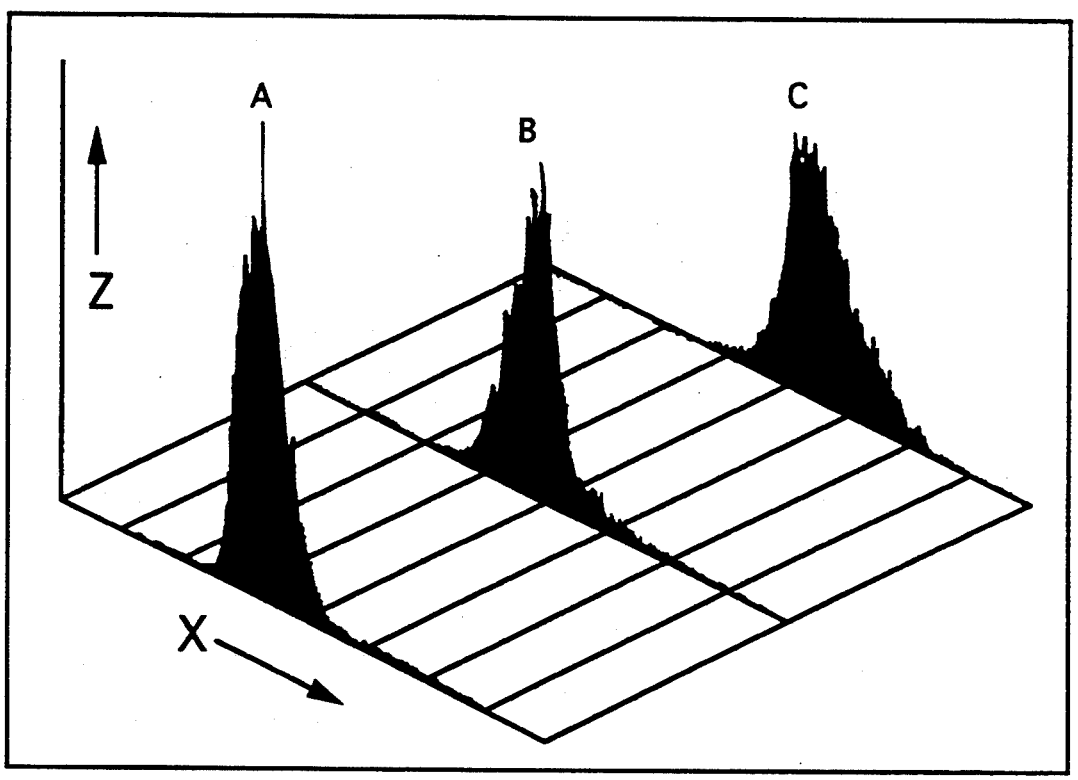
FIG. 4 illustrates. flow cytometric analysis of various cells labelled with FLM.

The intrinsic fluorescent of FLM was used to measure its cellular content in A-253, C-10E and C-10E$^R$ cells by flow cytometry. Cells were incubated with 100 μM FLM for 60 minutes at 37° C. and subjected to flow cytometric analysis as described herein. FIG. 4 shows the histogram distribution of log FLM content for the three cell lines following incubation of cells with FLM. The BLM-resistant C-10E cells (histogram A) were found to contain the least amount of FLM as measured by the mean fluorescent channel number (mean FL1=61). In contrast, the BLM-sensitive A-253 cells (histogram C) possessed 4-fold higher fluorescent intensity (mean FL1=250) and the C-10E$^R$ cells (histogram B) with relatively lower levels of BLM resistance, showed intermediate level of FLM (mean FL1=122). The cell diameter as measured by Coulter counter was similar for all the three cell lines (18-°μm). These results establish that fluorescent-labelled analogs of BLM and BLM derivatives, such as FLM, may be used to measure BLM-resistance/sensitivity and BLM derivative resistance/sensitivity in cells.

Example 4

Use of FLM to Quantify Cellular Level of BLM-like Drug Content

Exponentially growing A-253, C-10E or C-10E$^R$ cells were harvested and approximately $1.5 \times 10^6$ cells were incubated in 200 μl medium at 37° C. for 60 minutes in the presence or absence of 100 μM FLM. Drug incubation was terminated by washing the cells with $3 \times 1$ ml of ice-cold PBS, resuspending the cells in 1 ml of 50 mM bicarbonate buffer (pH=9.0) and lysing by sonication ($4 \times 5$ sec). The cell lysate was centrifuged at 12,000 rpm (Eppendorf Microcentrifuge 5415 C) to remove cellular debris, and the supernatant was filtered through 0.2 μm SPIN-X centrifuge filter unit (Costar, Cambridge, Mass.). The cell-associated fluorescent was measured using a fluorescent spectrophotometer. Autofluorescent associated with cells in the absence of drug treatment was measured and subtracted from the fluorescent value of the drug-treated group.

Figure 5:
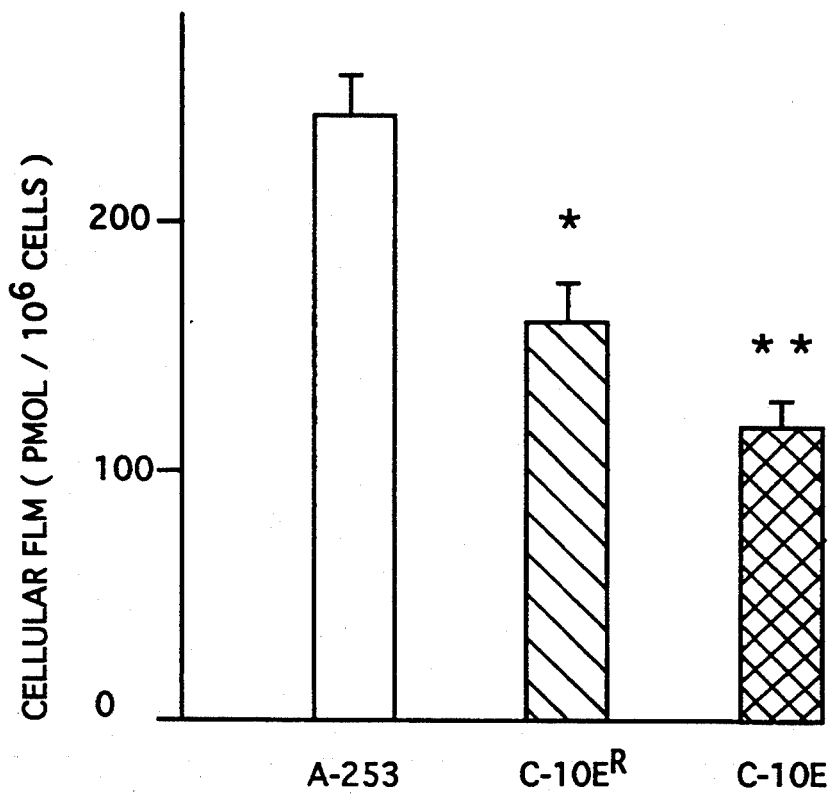
FIG. 5 illustrates the cellular association of FLM in various types of cells.

To quantify the levels of cell-associated FLM in A253, C-10E and C-10E$^R$ cell lines, cells were incubated with 100 μM FLM for 1 hour at 37° C. and the cellular fluorescent of the three cell lines were measured by fluorometry. FIG. 5 shows that A-253 cells exhibited 2-fold higher levels of cell-associated FLM (246 pmol/10$^6$ cells) when compared to C-10E cells (123 pmol/10$^6$ cells) whereas C-10E$^R$ cells contained intermediate levels of FLM (167 pmol/10$^6$ cells). These results are consistent with previous studies using [$^3$H]BLM A$_2$. See, Morris, G., et al., "Cysteine Proteinase Inhibitors and Bleomycin Sensitive and Resistant Cells," Biochem. Pharmacol., 41:1559–1566 (1991). Furthermore, when A-253 cells were incubated with 100 μM BLM A$_2$ or FLM for 1 hour at 37° C., the amount of cell-associated FLM was found to be approximately 2.5-fold higher than for BLM A$_2$ (255 pmol FLM/10$^6$ cells vs. 106 pmol BLM A$_2$/10$^6$ cells). A similar 2-fold difference in drug accumulation was seen when A-253 cells were incubated with 50 μM BLM A$_2$ or FLM for 1 hour at 37° C. This demonstrates that the difference in cellular accumulation of the two compounds, i.e. BLM A$_2$ and FLM, is independent of the concentration used for the incubation.

EXAMPLE 5

Use of FLM to Cleave DNA

The ability of various drugs to cause breakage of covalently closed circular DNA was determined using a slight modification of a previously described DNA cleavage assay. See, Lazo, J. S., et al, "Enhanced Bleomycin-induced DNA Damage and Cytotoxicity with Calmodulin Antagonists," Molec. Pharmacol., 27: 387–393, (1985). Metal-free FLM was first made by chelating the metal with dithizone using a previously described procedure. See, Roy, S. R., et al., "Chemical Synthesis of Radiolabeled Bleomycin A$_2$ and its Binding to DNA," Cancer Res., 41: 4471–4477, (1981), incorporated by reference herein. A comparison of DNA cleavage potency of FLM with that of BLM A$_2$ and TLM S$_{10b}$ was then made by incubating form I plasmid pGEM-3Z DNA (0.6 pmol) with various concentrations of the above drugs in a buffer containing 80 mM Tris-acetate (pH=8.0), 20 mM MgCl$_2$, 25 mM DTT and stoichiometric amounts of Fe(NH$_4$)$_2$(SO$_4$)$_2$ in a final volume of 25 μl The incubation was carried out for 20 min at 4° C. and stopped with the addition of 50 mM EDTA. The disappearance of form I DNA and the appearance of form II and form III DNA were assayed by gel electrophoresis with 1.2% agarose gels at room temperature for 15 h at 30 V in a buffer containing 40 mM Tris-acetate and 1 mM EDTA. The gel was then stained with 1 μg/ml ethidium bromide for 1 hour and the DNA visualized by UV irradiation. A negative film of the gel was recorded and scanned using an LKB 2400 GelScan XL densitometer. The effect of incubation time on cleavage of pGEM-3Z DNA by TLM S$_{10b}$ and FLM was also determined using equipotent amounts of TLM S$_{10b}$ and FLM (0.05 and 0.62 μM, respectively) by gel electrophoresis as described above.

The cytotoxic action of the BLM class of compounds is believed to result from a ternary Fe(II)-BLM-O$_2$ complex, which generates reactive oxygen radical species capable of cleaving DNA. See, Lown, J. W., "Newer Approaches to the Study of the Mechanisms of Action of Antitumor Antibiotics," *Acc. Chem. Res.*, 15: 381–387, (1982);, Stubbe, J., et al., "Mechanisms of Bleomycin Induced DNA Degradation," *Chem. Rev.*, 87: 1107–1136, (1987).

Figure 6A:
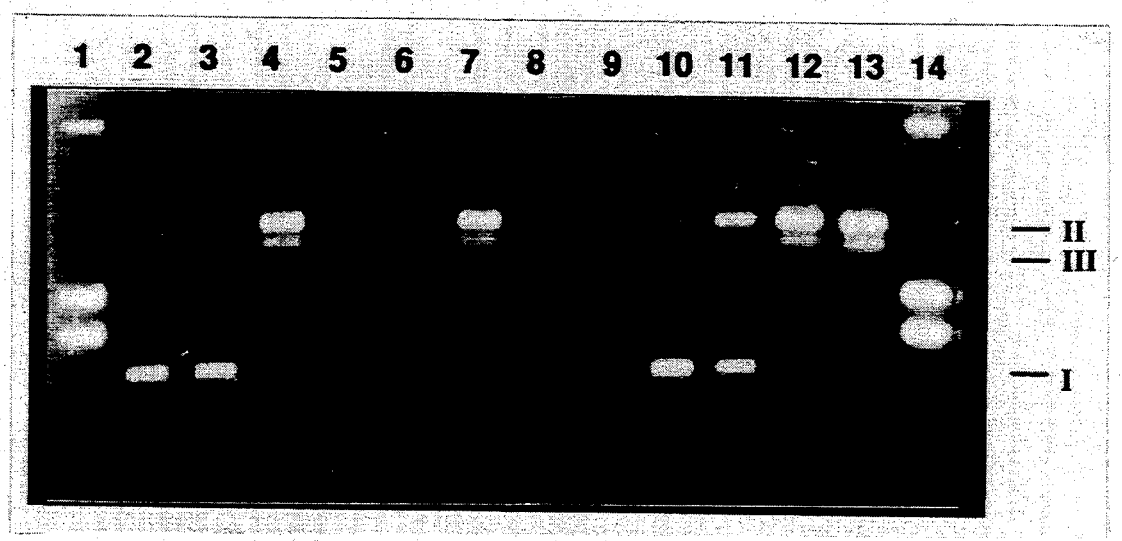
FIG. 6A is a photograph of an agarose gel which illustrates DNA cleavage by bleomycin and bleomycin derivatives, including FLM.
Figure 6B:
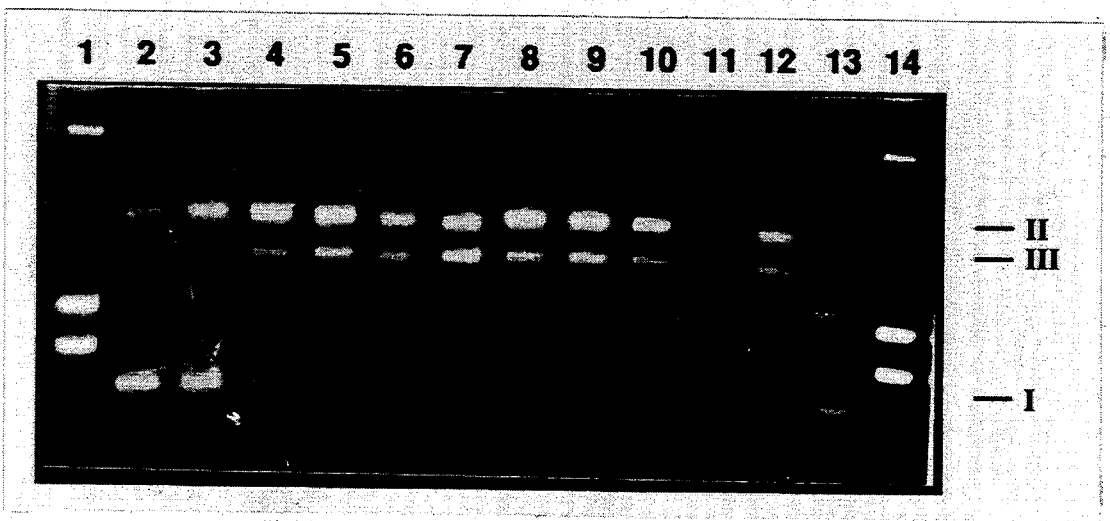
FIG. 6B is a photograph of an agarose gel which illustrates the effect of time on DNA cleavage by TLM $S_{10b}$ and FLM.

Covalently closed circular DNA was incubated with various concentrations of BLM $A_2$, TLM $S_{10b}$ and FLM for 20 minutes in the presence of stoichiometric amounts of Fe(II) to compare their ability to damage DNA. FIG. 6A shows the single- and double-strand DNA breaks caused by BLM $A_2$, TLM $S_{10b}$ and FLM. BLM $A_2$ was found to be approximately twice as potent as TLM $S_{10b}$. For example, 9.8 and 21.1% form I DNA remain undegraded following incubation with 0.05 μM BLM $A_2$(lane 4) and TLM $S_{10b}$ (lane 7), respectively. FLM was also able to cleave form I DNA, converting it, in a concentrationdependent manner, to forms II and III (lanes 10–13). However, it was 12 times less potent than TLM $S_{10b}$. The rate of DNA breakage by TLM $S_{10b}$ and FLM were compared, as shown in FIG. 6B. Equipotent concentrations of TLM $S_{10b}$ and FLM (0.05 and 0.62 μM, respectively) were incubated with form I DNA for 1, 5, 10, 20 and 30 minutes and the percent form I DNA remaining was calculated from densitometric scanning of the band corresponding to form I. Following incubation with FLM for 1 minute, only 6.5% form I DNA remained undegraded (lane 8). In contrast, 74% form I DNA remained intact following incubation with TLM $S_{10b}$ for 1 minute (lane 3) and 10 minutes incubation was required to cleave 95% of form I (lane 5). These data suggest that FLM exhibits an approximately 10 times greater rate of DNA cleavage relative to TLM $S_{10b}$ when equipotent doses are compared directly.

From the foregoing, it is apparent that the fluorescent-labelled bleomycin analog of the present invention may be employed in a variety of uses. For example, the analog may be used in a method of determining cellular content, uptake, and distribution of bleomycin or a bleomycin derivative, by exposing cells to the fluorescent-labelled bleomycin analog and measuring the cell-associated fluorescent of the cells with a fluorescent measuring device. Furthermore, FLM may be a unique reagent for identifying and isolating BLM-resistant and BLM-sensitive cells with an inherent or acquired property of reduced or enhanced BLM content.

It is also clear from the examples set forth herein that the fluorescent-labelled bleomycin analog of the invention may be used in a method of inhibiting cell growth by exposing cells to the analog for sufficient time and under appropriate conditions.

A further benefit of the invention is the use of the fluorescent-labelled bleomycin analog in a process of inhibiting cancerous cell growth in a patient, wherein the analog is provided in a dosage effective to resist cancerous cell growth in the patient and administered to the patient, either intravenously, intramuscularly, or subcutaneously. The effective dosage would be analogous to dosages for the non-fluorescent-labelled bleomycin or bleomycin derivatives, for example, BLENOXANE® or TLM $S_{10b}$. Of course, as is known to those skilled in the art, therapeutically effective dosages are variable, and based on, for example, purpose of use, weight of the patient, surface area of the patient and other known variables. Preferred concentrations of use of the fluorescent-labelled analogs of bleomycin or bleomycin derivatives of the invention are about 0.001 to 200 μM, and when used in human patients, at a maximum dosage of about 0.0001 to 3 mg/kg per day.

Whereas, particular embodiments of the invention have been described above for purposes of illustration, it will be evident to those skilled in the art that numerous variations of the details may be made without departing from the invention as defined in the following claims.

We claim:

1. A fluorescent probe for detecting the intracellular uptake and distribution of a talisomycin, said probe being a fluorescent-labelled analogue which is a covalently linked product of said talisomycin having the structure

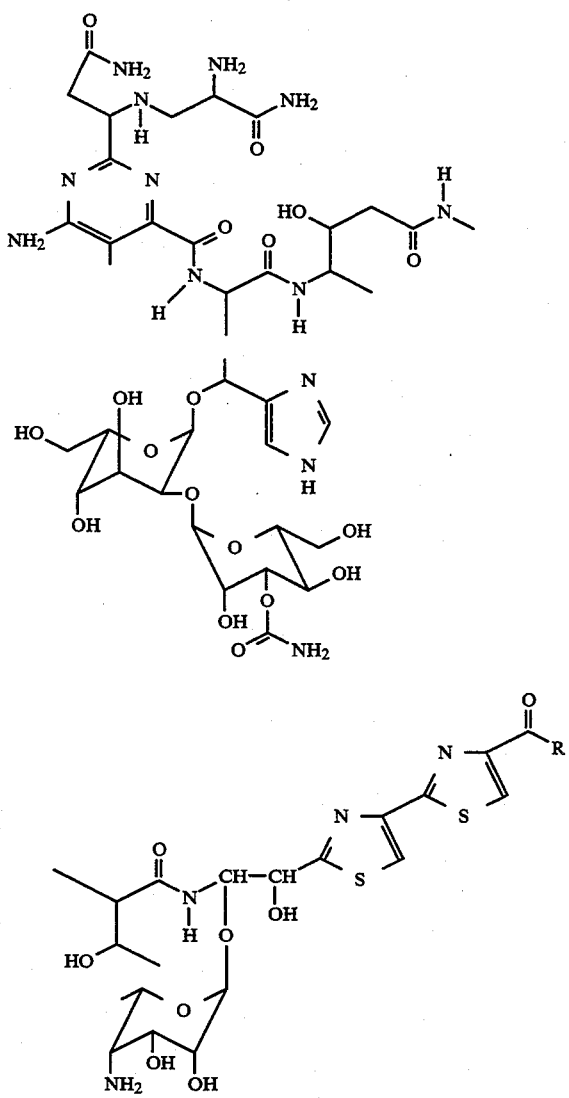

where R=NH—$(CH_2)_3$—CH($NH_2$)—$CH_2$—CO—NH—$(CH_2)_3$—NH$(CH_2)_4$—$NH_2$; NH—$(CH_2)_3$—NH—$(CH_2)_4NH_2$; or NH—$(CH_2)_4$—$NH_2$ and a fluorescent moiety, said fluorescent moiety being present in said product in a quantity of one molecule of said fluorescent moiety attached to said R group at the terminal amine of said talisomycin, said fluorescent-labelled analogue exhibiting a fluorescence intensity about 300–400 times greater than said talisomycin, said probe being characterized by retaining substantially the same biological properties as said talisomycin and being adapted to ascertain the content, uptake and distribution of said talisomycin in living cells.

2. The fluorescent probe of claim 1 wherein said fluorescent moiety is selected from the group consisting of fluorescein, 4-halo-7-nitrobenzo-2-oxa-1,3, diazole (NBD), 4,4-difluoro-5,7-dimethyl-4-bora-3a,4a-diaza-S-indacene-3-propionic acid (BODIPY), pyrene, tetramethylrhodamine and cyanine dyes.

3. A fluorescent probe for detecting the intracellular uptake and distribution of a bleomycin, said probe being a fluorescent-labelled analogue which is a convalently linked product of said bleomycin having the structure

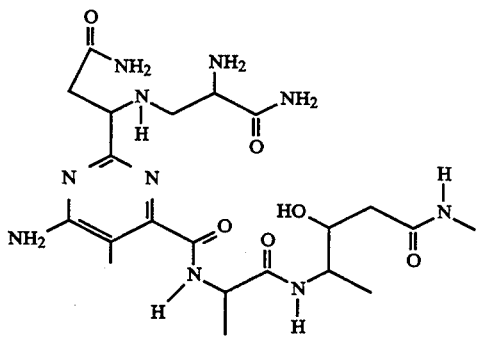

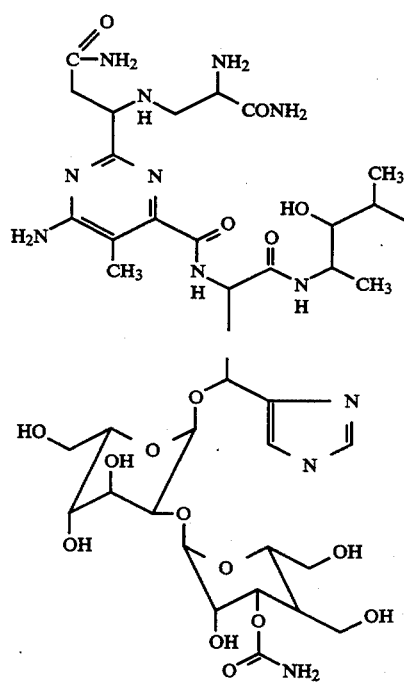

(1)

where R=OH; NH—(CH2)3—S—CH3; NH—(CH2)3—NH2; or NH—(CH2)3—NH—(CH2)4—NH2 and a fluorescent moiety, said fluorescent moiety being present in said product in a quantity of one molecule of said fluorescent moiety attached to said R group at the terminal amine of said bleomycin, said fluorescent-labelled analogue exhibiting a fluorescence intensity about 300–400 times greater than said bleomycin, said probe being characterized by retaining substantially the same biological properties as said bleomycin and being adapted to ascertain the content, uptake and distribution of said bleomycin in living cells.

4. The fluorescent probe of claim 3 wherein said fluorescent moiety is selected from the group consisting of fluorescein, 4-halo-7-nitrobenzo-2-oxa-1,3, diazole (NBD), 4,4-difluoro-5,7-dimethyl-4-bora-3a, 4a-diaza-S-indacene-3-propionic acid (BODIPY), pyrene, tetramethylrhodamine and cyanine dyes.

5. A fluorescent probe for detecting the intracellular uptake and distribution of a talisomycin, said probe being a fluorescent-labelled analogue which is a covalently linked product of said talisomycin having the structure

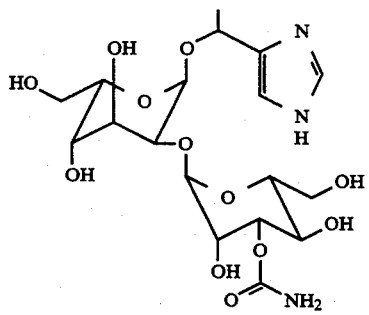

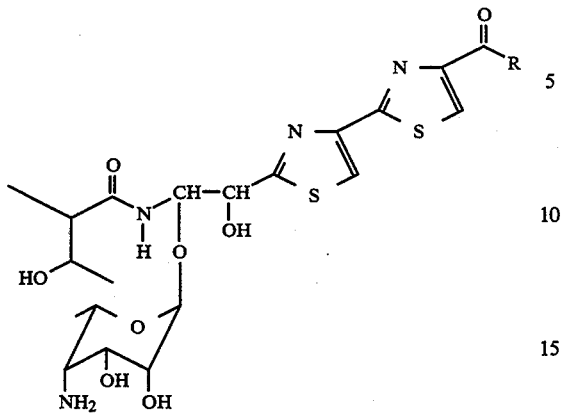

where R=NH—(CH₂)₃—CH(NH₂)—CH₂—CO—NH—(CH₂)₃—NH(CH₂)₄—NH₂; NH—(CH₂)₃—NH—(CH₂)₄NH₂; or NH—(CH₂)₄—NH₂ and a fluorescent moiety, said fluorescent moiety being present in said product in a quantity of one molecule of said fluorescent moiety attached to said R group at the terminal amine of said talisomycin, said fluorescent-labelled analogue exhibiting a fluorescence intensity about 300–400 times greater than said talisomycin, said probe being characterized by retaining substantially the same biological properties as said talisomycin and being adapted to ascertain the content, uptake and distribution of said talisomycin in living cells, and wherein retention of said biological properties of talisomycin facilitates fragmentation of DNA in said living cells.

6. A fluorescent probe for detecting the intracellular uptake and distribution of a talisomycin, said probe being a fluorescent-labelled analog which is a covalently linked product of said talisomycin having the structure

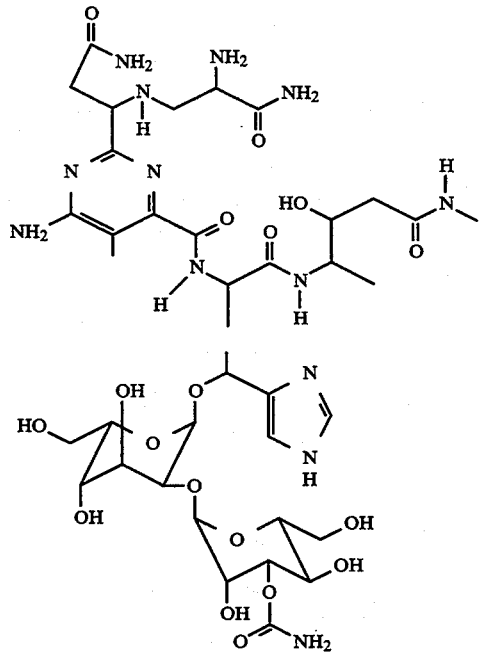

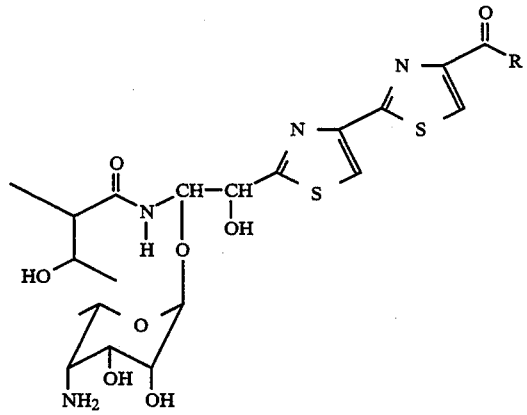

where R=NH—(CH₂)₃—CH(NH₂)—CH₂—CO—NH—(CH₂)₃—NH(CH₂)₄—NH₂; NH—(CH₂)₃—NH—(CH₂)₄NH₂; or NH—(CH₂)₄—NH₂ and a fluorscent moiety, said fluorescent moiety being present in said product in a quantity of one molecule of said fluorescent moiety attached to said R group at the terminal amine of said talisomycin, said fluorescent-labelled analogue exhibiting a fluorescence intensity about 300–400 times greater than said talisomycin, said probe being characterized by retaining substantially the same biological properties as said talisomycin and being adapted to ascertain the content, uptake and distribution of said talisomycin in living cells, and wherein retention of said biological properties of talisomycin facilitates wherein said fluorescent moiety is selected from the group inhibition of cell growth.

7. A fluorescent probe for detecting the intracellular uptake and distribution of a talisomycin, said probe being a fluorescent-labelled analogue which is a covalently linked product of said talisomycin having the structure

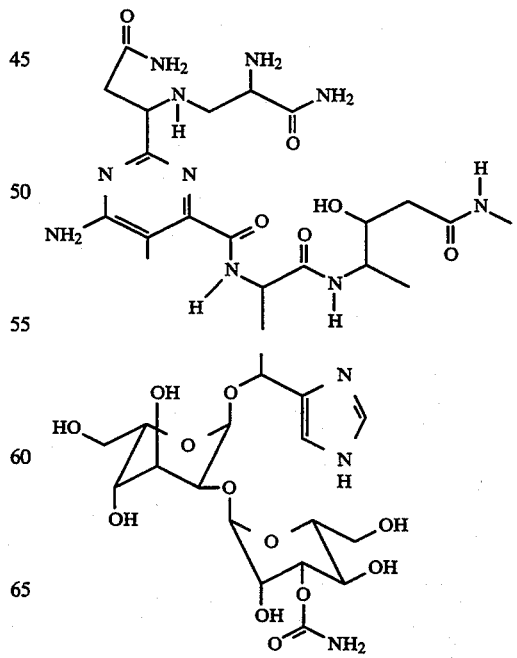

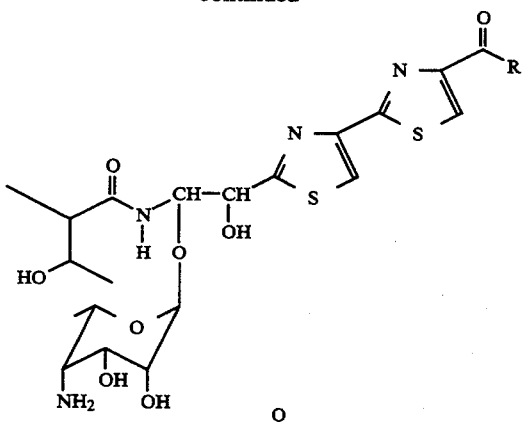

where R=NH—(CH₂)₃—CH(NH₂)—CH₂—CO—NH—(CH₂)₃—NH(CH₂)₄—NH₂; NH—(CH₂)₃—NH—(CH₂)₄NH₂; or NH—(CH₂)₄—NH₂ and a fluorescent moiety, said fluorescent moiety being present in said product in a quantity of one molecule of said fluorescent moiety attached to said R group at the terminal amine of said talisomycin, said fluorescent-labelled analogue exhibiting a fluorescence intensity about 300–400 times greater than said talisomycin, said probe being characterized by retaining substantially the same biological properties as said talisomycin and being adapted to ascertain the content, uptake and distribution of said talisomycin in living cells, and wherein retention of said biological properties of talisomycin facilitates measurement of sensitivity and resistance to talisomycin in living cells.

8. A fluorescent probe for detecting the intracellular uptake and distribution of a bleomycin, said probe being a fluorescent-labelled analogue which is a covalently linked product of said bleomycin having the structure

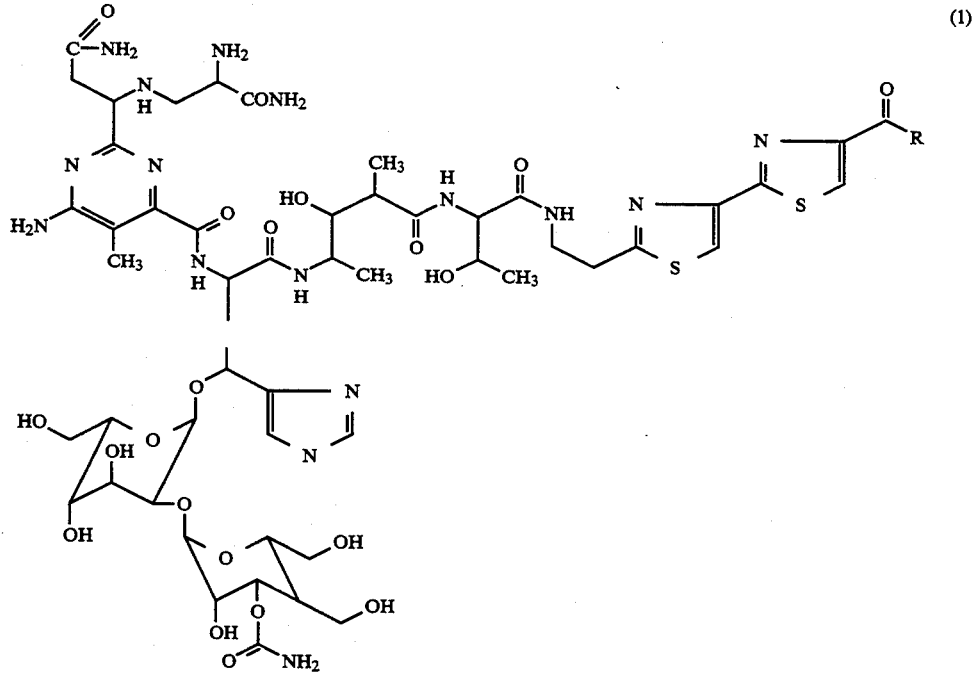

(1)

where R=OH; NH—(CH₂)₃—S—CH₃; NH—(CH₂)₃—NH₂; or NH—(CH₂)₃—NH—(CH₂)₄—NH₂ and a fluorescent moiety, said fluorescent moiety being present in said product in a quantity of one molecule of fluorescent moiety attached to said R group at the terminal amine of said bleomycin, the analogue exhibiting a fluorescence intensity about 300–400 times greater than said bleomycin, said probe being characterized by retaining substantially the same biological properties as said bleomycin and being adapted to ascertain the content, uptake and distribution of said bleomycin in living cells, and wherein retention of said biological properties of bleomycin facilitates fragmentation of DNA in said living cells.

9. A fluorescent probe for detecting the intracellular uptake and distribution of a bleomycin, said probe being a fluorescent-labelled analogue which is a covalently linked product of said bleomycin having the structure

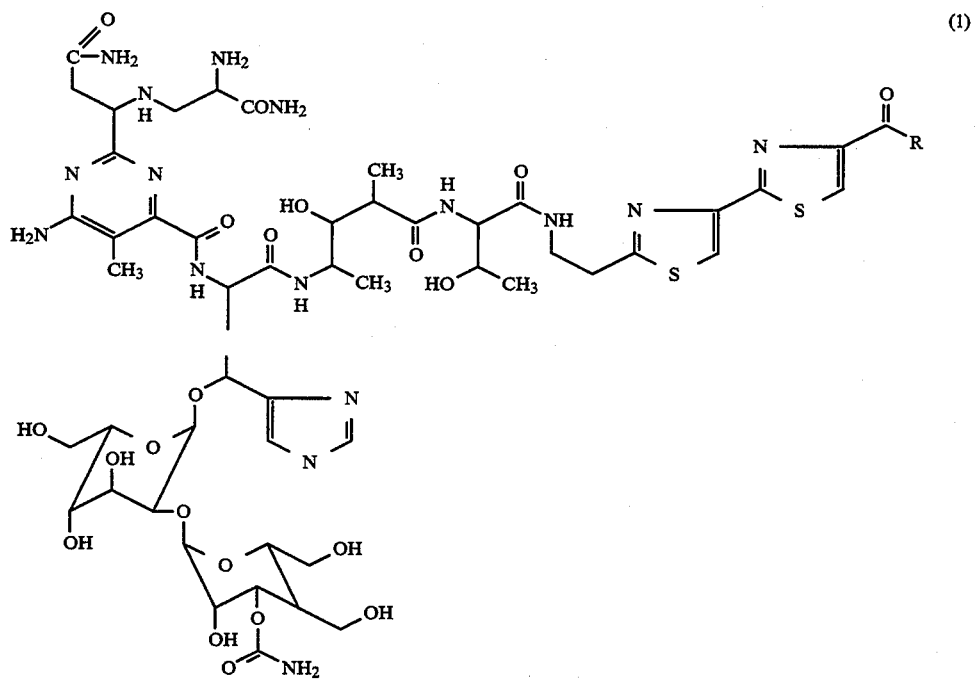

where R=OH; NH—(CH$_2$)$_3$—S—CH$_3$; NH—(CH$_2$)$_3$—NH—(CH$_2$)$_4$—NH$_2$ and a fluorescent moiety, said fluorescent moiety being present in said product in a quantity of one molecule of fluorescent moiety attached to said R group at the terminal amine of said bleomycin, the analogue exhibiting a fluorescence intensity about 300–400 times greater than said bleomycin, said probe being characterized by retaining substantially the same biological properties as said bleomycin and being adapted to ascertain the content, uptake and distribution of said bleomycin in living cells, and wherein retention of said biological properties of bleomycin facilitates inhibition of cell growth.

10. A fluorescent probe for detecting the intracellular uptake and distribution of a bleomycin, said probe being a fluorescent-labelled analogue which is a covalently linked product of said bleomycin having the structure

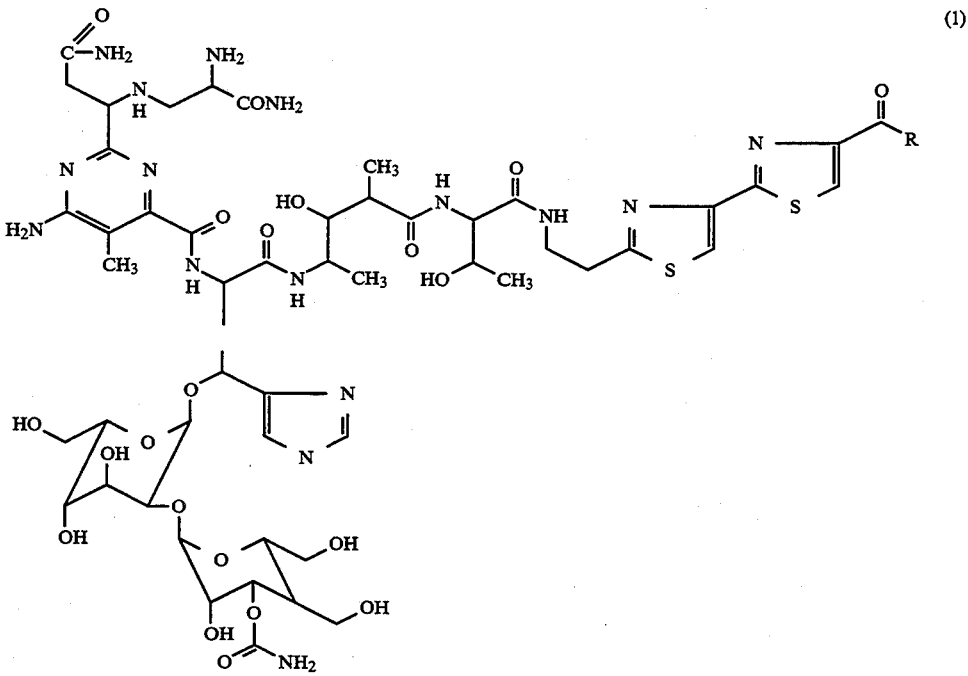

where R=OH; NH—(CH$_2$)$_3$—S—CH$_3$; NH—(CH$_2$)$_3$—NH$_2$; or NH—(CH$_2$)$_3$—NH—(CH$_2$)$_4$—NH$_2$ and a fluorescent moiety, said fluorescent moiety being present in said product in a quantity of one molecule of fluorescent moiety attached to said R group at the terminal amine of said bleomycin, the analogue exhibiting a fluorescence intensity about 300–400 times greater than said bleomycin, said probe being characterized by retaining substantially the same biological properties as said bleomycin and being adapted to ascertain the content, uptake and distribution of said bleomycin in living cells, and wherein retention of said biological properties of bleomycin facilitates measurement of sensitivity and resistance to bleomycin in living cells.

11. The fluorescent probe of claim 1 made by a process comprising:
   a. providing talisomycin;
   b. preparing a metal complex of said talisomycin in solution;
   c. buffering said metal complex containing solution with buffered means;
   d. adding a buffered fluorescent moiety-containing solution to said buffered metal complex-containing solution;
   e. mixing said solutions; and
   f. recovering a fluorescent-labelled derivative of talisomycin.

12. The fluorescent probe of claim 11 wherein the metal in step b. is selected from the group consisting of Zn, Cu, Cd and Co and preparing said metal complex by adding a salt of said metal to an aqueous solution of said talisomycin.

13. The fluorescent probe of claim 3 made by a process comprising:
   a. providing bleomycin;
   b. preparing a metal complex of said bleomycin in solution;
   c. buffering said metal complex containing solution with buffered means;
   d. adding a buffered fluorescent moiety-containing solution to said buffered metal complex-containing solution;
   e. mixing said solutions; and
   f. recovering a fluorescent-labelled derivative of bleomycin.

14. The fluorescent probe of claim 11 wherein the metal in step b. is selected from the group consisting of Zn, Cu, Cd and Co and preparing said metal complex by adding a salt of said metal to an aqueous solution of said bleomycin.

* * * * *

UNITED STATES PATENT AND TRADEMARK OFFICE
CERTIFICATE OF CORRECTION

PATENT NO. : 5,420,228
DATED : May 30, 1995
INVENTOR(S) : JOHN S. LAZO et al.

It is certified that error appears in the above-identified patent and that said Letters Patent is hereby corrected as shown below:

In column 1, line 43, "(2989)" should be --(1989)--.

In column 5, line 17, "$S_{106}$" should be --$S_{10b}$--.

In column 16, lines 57, 64 and 67, "C-10E ®" should be --$C-10E^R$--.

In column 18, line 9, "106" should be --$10^6$--.

In column 19, line 16, "concentrationdependent" should be --concentration-dependent--.

In claim 6, column 24, lines 21-22, "fluorscent" should be --fluorescent--.

Signed and Sealed this

Thirtieth Day of July, 1996

Attest:

BRUCE LEHMAN

Attesting Officer    Commissioner of Patents and Trademarks